(12) United States Patent
Presta et al.

(10) Patent No.: US 8,524,217 B2
(45) Date of Patent: *Sep. 3, 2013

(54) MCP1-IG FUSION VARIANTS

(75) Inventors: Leonard G. Presta, San Francisco, CA (US); Chuan-Chu Chou, Westfield, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 209 days.

This patent is subject to a terminal disclaimer.

(21) Appl. No.: 13/105,453

(22) Filed: May 11, 2011

(65) Prior Publication Data

US 2011/0280873 A1    Nov. 17, 2011

Related U.S. Application Data

(60) Provisional application No. 61/333,447, filed on May 11, 2010.

(51) Int. Cl.
*C07K 14/52* (2006.01)
*A61K 38/19* (2006.01)

(52) U.S. Cl.
USPC ........ 424/85.1; 424/134.1; 530/351; 530/402

(58) Field of Classification Search
None
See application file for complete search history.

(56) References Cited

U.S. PATENT DOCUMENTS

| | | | |
|---|---|---|---|
| 4,588,585 A | 5/1986 | Mark et al. |
| 4,751,180 A | 6/1988 | Cousens et al. |
| 5,098,833 A | 3/1992 | Lasky et al. |
| 5,116,964 A | 5/1992 | Capon et al. |
| 5,179,078 A | 1/1993 | Rollins et al. |
| 5,212,073 A | 5/1993 | Rollins et al. |
| 5,216,131 A | 6/1993 | Lasky et al. |
| 5,225,538 A | 7/1993 | Capon et al. |
| 5,278,287 A | 1/1994 | Rollins et al. |
| 5,359,046 A | 10/1994 | Capon et al. |
| 5,428,130 A | 6/1995 | Capon et al. |
| 5,455,165 A | 10/1995 | Capon et al. |
| 5,459,128 A | 10/1995 | Rollins et al. |
| 5,514,582 A | 5/1996 | Capon et al. |
| 5,532,144 A | 7/1996 | Yoshimura et al. |
| 5,571,713 A | 11/1996 | Lyle et al. |
| 5,605,671 A | 2/1997 | Lyle et al. |
| 5,705,360 A | 1/1998 | Rollins et al. |
| 5,714,147 A | 2/1998 | Capon et al. |
| 5,714,578 A | 2/1998 | Yoshimura et al. |
| 5,739,103 A | 4/1998 | Rollins et al. |
| 5,840,844 A | 11/1998 | Lasky et al. |
| 5,854,412 A | 12/1998 | Rollins et al. |
| 5,932,703 A | 8/1999 | Godiska et al. |
| 6,001,567 A | 12/1999 | Brow et al. |
| 6,090,795 A | 7/2000 | Yoshimura et al. |
| 6,403,782 B1 | 6/2002 | Luster et al. |
| 6,406,697 B1 | 6/2002 | Capon et al. |
| 6,485,910 B1 | 11/2002 | Walker et al. |
| 6,498,015 B1 | 12/2002 | Godiska et al. |
| 6,569,418 B1 | 5/2003 | Garzino-Demo et al. |
| 6,590,075 B2 | 7/2003 | Ruben et al. |
| 6,607,879 B1 | 8/2003 | Cocks et al. |
| 6,706,471 B1 | 3/2004 | Brow et al. |
| 6,737,513 B1 | 5/2004 | Gray et al. |
| 6,767,535 B1 | 7/2004 | Rollins et al. |
| 6,780,973 B1 | 8/2004 | Luster et al. |
| 6,780,982 B2 | 8/2004 | Lyamichev et al. |
| 6,787,645 B1 | 9/2004 | Rollins et al. |
| 6,869,924 B1 | 3/2005 | Yoshimura et al. |
| 6,878,687 B1 | 4/2005 | Ruben et al. |
| 7,713,521 B2 | 5/2010 | Chou et al. |
| 7,972,591 B2 | 7/2011 | Chou et al. |
| 8,282,914 B2 | 10/2012 | Chou et al. |
| 2002/0009724 A1 | 1/2002 | Schlegel et al. |
| 2002/0009730 A1 | 1/2002 | Chenchik et al. |
| 2002/0137081 A1 | 9/2002 | Bandman |
| 2002/0198362 A1 | 12/2002 | Gaiger et al. |
| 2003/0073144 A1 | 4/2003 | Benson et al. |
| 2003/0078396 A1 | 4/2003 | Gaiger et al. |
| 2003/0099974 A1 | 5/2003 | Lillie et al. |
| 2003/0129214 A1 | 7/2003 | Bornstein et al. |
| 2003/0143220 A1 | 7/2003 | Capon et al. |
| 2003/0162737 A1 | 8/2003 | Egashira et al. |
| 2003/0166903 A1 | 9/2003 | Astromoff et al. |
| 2003/0175704 A1 | 9/2003 | Lasek et al. |
| 2004/0002068 A1 | 1/2004 | Gaiger et al. |
| 2004/0029179 A1 | 2/2004 | Koentgen |
| 2004/0031072 A1 | 2/2004 | La Rosa et al. |
| 2004/0077835 A1 | 4/2004 | Offord et al. |
| 2004/0110792 A1 | 6/2004 | Raponi |
| 2004/0157253 A1 | 8/2004 | Xu et al. |
| 2004/0177387 A1 | 9/2004 | Jayakrishna |
| 2004/0224875 A1 | 11/2004 | Schilling et al. |

(Continued)

FOREIGN PATENT DOCUMENTS

| | | |
|---|---|---|
| CA | 2152141 | 12/1996 |
| CA | 2343602 | 10/2001 |

(Continued)

OTHER PUBLICATIONS

The Merck Manual of Diagnosis and Therapy (1999), Beers and Berkow, 17$^{th}$ edition, pp. 1654-1658.
Chintalacharuvu et al. Hybrid IgA2/IgG1 antibodies with tailor-made effector functions. Clin Immunol. Oct. 2001;101(1):21-31.
Esposito & Chatterjee. Enhancement of soluble protein expression through the use of fusion tags. Curr Opin Biotechnol. Aug. 2006;17(4):353-358.
Ferrara et al. Vascular endothelial growth factor is essential for corpus luteum angiogenesis. Nat Med. Mar. 1998;4(3):336-340.
Gerber et al. VEGF couples hypertrophic cartilage remodeling, ossification and angiogenesis during endochondral bone formation. Nat Med. Jun. 1999;5(6):623-628.
Hilbert et al. Pharmacokinetics ABS pharmacodynamics of BIWH 3 in healthy duffy antigen positive and duffy antigen negative male volunteers. Am. Soc. Clin. Pharm. Therap. 2006, PII-60.
Holash et al. VEGH-Trap: a VEGF blocker with potent antitumor effects. Proc Natl Acad Sci U S A. Aug. 20, 2002;99(17):11393-8.

(Continued)

Primary Examiner — Prema Mertz

(57) ABSTRACT

The present invention provides, in part, MCP1-Ig fusion polypeptides exhibiting surprisingly beneficial properties as well as methods for treating various diseases (e.g., inflammatory diseases) by administering any of such fusions.

10 Claims, No Drawings

(56) References Cited

U.S. PATENT DOCUMENTS

| | | |
|---|---|---|
| 2004/0248169 A1 | 12/2004 | Liew |
| 2004/0265808 A1 | 12/2004 | Garcia et al. |
| 2005/0058635 A1 | 3/2005 | Demuth et al. |
| 2005/0058639 A1 | 3/2005 | Gudas et al. |
| 2005/0232923 A1 | 10/2005 | Yan et al. |
| 2006/0263774 A1 | 11/2006 | Clark et al. |

FOREIGN PATENT DOCUMENTS

| | | |
|---|---|---|
| CN | 1144845 | 5/2000 |
| CN | 1435433 | 8/2003 |
| JP | 2003310272 | 11/2003 |
| JP | 2004307427 | 11/2004 |
| WO | WO90/07863 | 7/1990 |
| WO | WO92/19737 | 11/1992 |
| WO | WO95/04158 | 2/1995 |
| WO | WO95/09232 | 4/1995 |
| WO | WO95/13295 | 5/1995 |
| WO | WO95/19167 | 7/1995 |
| WO | WO98/45435 | 10/1998 |
| WO | WO99/05297 | 2/1999 |
| WO | WO99/12968 | 3/1999 |
| WO | WO00/04926 | 2/2000 |
| WO | WO00/09525 | 2/2000 |
| WO | WO00/21991 | 4/2000 |
| WO | WO00/42071 | 7/2000 |
| WO | WO01/46697 | 6/2001 |
| WO | WO02/18413 | 3/2002 |
| WO | WO02/066510 | 8/2002 |
| WO | WO02/068579 | 9/2002 |
| WO | WO02/085308 | 10/2002 |
| WO | WO02/085309 | 10/2002 |
| WO | WO03/037376 | 5/2003 |
| WO | WO03/082920 | 10/2003 |
| WO | WO03/083059 | 10/2003 |
| WO | WO03/084993 | 10/2003 |
| WO | WO03/091391 | 11/2003 |
| WO | WO2004/022778 | 3/2004 |
| WO | WO2004/031233 | 4/2004 |
| WO | WO2004/065545 | 8/2004 |
| WO | WO2004/078777 | 9/2004 |
| WO | WO2004/080273 | 9/2004 |
| WO | WO2004/092368 | 10/2004 |
| WO | WO2004/096850 | 11/2004 |
| WO | WO2004/097052 | 11/2004 |
| WO | WO2004/112829 | 12/2004 |
| WO | WO2004/113522 | 12/2004 |
| WO | WO2005/002416 | 1/2005 |
| WO | WO2005/037305 | 4/2005 |
| WO | WO2007/113285 | 10/2007 |

OTHER PUBLICATIONS

Kurlander & Batker. The binding of human immunoglobulin G1 monomer and small, covalently cross-linked polymers of immunoglobulin G1 to human peripheral blood monocytes and polymorphonuclear leukocytes. J Clin Invest, Jan. 1982;69(1):1-8.
Ohtsuki et al. Detection of monocyte chemoattractant protein-1 receptor expression in experimental atherosclerotic lesions: an autoradiographic study. Circulation. Jul. 10, 2001;104(2):203-208.
Pashine et al. Failed efficacy of soluble human CD83-lg in allogeneic mixed lymphocyte reactions and experimental autoimmune encephalomyelitis: Implications for a lack of therapeutic potential. Immunol Lett. Jan. 15, 2008;115(1):9-15. Epub Nov. 29, 2007.
Saphire et al, Contrasting IgG structures reveal extreme asymmetry and flexibility. J Mol Biol. May 24, 2002;319(1):9-18.
Nigrovic PA, Lee DM Mast cells in inflammatory arthritis, Arthritis Res Ther, 2005:7(1):1-11, Epub Nov. 2, 2004.
Genbank accession No. BC025985 (released Mar. 22, 2002).
Genbank accession No. BC057688 (released Sep. 16, 2003).
Genbank accession No. NM002982; derived from S71513.1 (released May 7, 1993).
Genbank accession No. NM009915; derived from U56819.1 (released Sep. 12, 1996).
Genbank accession No. NM006274; derived from AB000887.1 (released Jun. 6, 1997).
Genbank accession No. NP002975; derived from AY766446.1 (released Oct. 1, 2005).
Genbank accession No. NP006265; derived from AB000887.1 (released Jun. 6, 1997).
Genbank accession No. NP954637; derived from BC031072.1 (released Jun. 13, 2002).
Brodmerkel, Carrie M., et al.; "Discovery and Pharmacological Characterizatin of a Novel Rodent-Active CCR2 Antagonist, INCB3344"; The Journal of Immunology; 175:5370-5378 (2005).
Chou, Chuan-Chu, et al.; "Pharmacological characterization of the chemokine receptor, hCCR1 in a stable transfectant and differentiated HL-60 cells: antagonism of hCCR1 activation by MIP-1.beta."; British Journal of Pharmacology; 137:663-675 (2002).
Conti, Ilaria, et al.; "CCL2 (Monocyte Chemoattractant Protein-1) and Cancer"; Seminars in Cancer Biology; 14:149-154 (2004).
Lu, Bao, et al . ; "Abnormalities in monocyte recruitment and cytokine expression in monocyte chemoattractant protein 1-deficient mice" J Exp Med. Feb. 16, 1998;187(4):601-608.
Neels, Jaap G., et al.; "Inflamed fat: what starts the fire?"; The Journal of Clinical Investigation; 116(1):33-35, (2006).
Sartipy, Peter, et al.; "Monocyte chemoattractant protein 1 in obesity and insulin resistance"; PNAS; 100(12):7265-7270, (2003).
Weisberg, Stuart P., et al.; "CCR2 modulates inflammatory and metabolic effects of high-fat feeding." J Clin Invest. Jan. 2006; 116(1):115-124. Epub Dec. 8, 2005.
Xu, Yuanyuan, et al.; "Residue at position 331 in the IgG1 and IgG4 CH2 domains contributes to their differential ability to bind and activate complement"; J Biol Chem.; 269(5):3469-3474, (1994).
Yoshimura, Teizo el al. "Human monocyte chemoattractant protein-1 (MCP-1). Full-length cDNA cloning, expression in mitogen-stimulated blood mononuclear leukocytes, and sequence similarity to mouse competence gene JE" FEBS Lett.; 244(2):487-493 (1989).
Zijlmans, H. Imaa, et al.; "The absence of CCL2 expression in cervical carcinoma is associated with increased survival and loss of heterozygosity at 17q11.2", Journal of Pathology; 208:507-517, (2006).
Charo, Israel F., et al., "Chemokines in the Pathogenesis of Vascular Disease", Circulation Research 95:858-866, (2004).
Francis, G.E., et al., PEGylation of cytokines and other therapeutic proteins and peptides: the importance of biological optimisation of coupling techniques, International Journal of Hematology, 68:1-18, (1998).
Gu, Long, et al.; "Control of T.sub.H2 polarization by the chemokine monocyte chemoattractant protein-1"; Nature; 404:407-411 (2000).
Jefferis, Roy, et al.; "Interaction sites on human IgG-Fc for FegammaR: current models"; Immunol Lett.; 82(1-2):57-65 (2002).
Kennedy, Kevin, J., et al.; "Acute and relapsing experimental autoimmune encephalomyelitis are regulated by differential expression of the CC chemokines macrophage inflammatory protein-1.alpha. and monocyte chemotactic protein-1"; Journal of Neuroimmunology; 92:98-108 (1998).
Huang, Deren, et al ., Absence of Monocyte Chemoattractant Protein 1 in Mice Leads to Decreased Local Macrophage Recruitment and Antigen-specific T Helper Cell Type 1 immune Response in Experimental Autoimmune Encephalomyelitis, Journal of Exp. Med., 193 (6):713-725 (2001).
Izikson, Leonid, et al., Resistance to Experimental Autoimmune Encephalomyelitis in Mice Lacking the CC Chemokine Receptor (CCR) 2, Journal of Exp. Med., 192(7):1075-1080 (2000).
Krautwald, Stefan, et al., Ectopic expression of CCL19 impairs alloimmune response in mice, Immunology, 112:301-309 (2004).
Mahad, Don J., et al., The role of MCP-1 (CCL2) and CCR2 in multiple sclerosis and experimental autoimmune encephalomyelitis (EAE), Seminars in Immunology, 15:23-32 (2003).
Quinones, Marlon P., et al., Experimental arthritis in CC chemokine receptor 2-null mice closely mimics severe human rheumatoid arthritis, The Journal of Clinical Investigation, 113(6):856-866 (2004).
International Search Report, International Application No. PCT/US2006/031155, Date of Mailing Dec. 12, 2006.
Genbank record No. NM000648. *Homo sapiens* chemokine (C-C motif) receptor 2 (CCR2), transcript variant B, mRNA. Mar. 15, 2009.

Gu L, Okada Y, Clinton SK, Gerard C, Sukhova GK, Libby P, Rollins BJ. Absence of monocyte chemoattractant protein-1 reduces atherosclerosis in low density lipoprotein receptor-deficient mice. Mol Cell. Aug. 1998;2(2):275-281.

Taub DD. Chemokine-leukocyte interactions. The voodoo that they do so well. Cytokine Growth Factor Rev. Dec. 1996;7(4):355-376.

Terpe. Overview of tag protein fusions: from molecular and biochemical fundamentals to commercial systems. Appl Microbiol Biotechnol. Jan. 2003;60(5):523-533.

Unanue & Benacerraf. Textbook of Immunology (2d ed.). Williams & Wilkins, Baltimore/London, 1984. pp. 46-51.

Galimberti D, Bresolin N, Scarpini E., Chemokine network in multiple sclerosis: role in pathogenesis and targeting for future treatments, Expert Rev Neurother, May 2004;4(3):439-453.

Elhofy, Adam, et al.; "Transgenic expression of CCL2 in the central nervous system prevents experimental autoimmune encephalomyelitis"; Journal of Leukocyte Biology; 77:229-237.

Fan, Xuedong, et al.; "Molecular cloning of a gene selectively induced by gamma interferon from human macrophage cell line U937"; Mol. Cell. Biol.; 9(5):1922-1928.

Grewal, Iqbal S., et al.; "Transgenic Monocyte Chemoattractant Protein-1 (MCP-1) in Pancreatic Islets Produces Monocyte-Rich Insulitis Without Diabetes"; The Journal of Immunology; 159:401-408 (1997).

Gu, Long, et al.; "In vivo properties of monocyte chemoattractant protein-1"; Journal of Leukocyte Biology; 62:577-580 (1997).

MCP1-IG FUSION VARIANTS

The present application claims the benefit of U.S. provisional patent application No. 61/333,447 filed on May 11, 2010 which is herein incorporated by reference in its entirety.

FIELD OF THE INVENTION

The present invention relates to fusion proteins that are useful for, inter alia, treatment or prevention of inflammatory conditions; along with method for treating such conditions using the fusion proteins.

BACKGROUND OF THE INVENTION

Expression and cellular localization of MCP1 (CCL2), e.g., in MS has been described in the various locations including the CNS. Evidence has established a role for MCP1 in the recruitment of inflammatory infiltrate into the CNS. Hence, MCP1 may be a target for specific and effective treatment in multiple sclerosis (MS). Multiple sclerosis is an inflammatory demyelinating disease of the human central nervous system (CNS). In MS, CNS inflammation is associated with demyelination and axonal degeneration, which leads to clinical presentation.

Exposure of circulating immune cells expressing the MCP1 receptor (CCR2) that typically mediate inflammatory diseases such as MS to continuously high circulating levels of MCP1 has been shown to desensitize such cells to the chemoattractant properties of the protein released from the tissue. For example, fusing the protein to an immunoglobulin so as to increase its half-life in the body of a subject has been shown to very effectively desensitize the cells (see US2007/0036750 A1).

SUMMARY OF THE INVENTION

The present invention provides an isolated polypeptide comprising MCP1 fused to a polypeptide linker which is fused to a human immunoglobulin gamma-1 variant polypeptide comprising the immunoglobulin hinge to the immunoglobulin CH3 region; wherein the linker comprises an amino acid sequence set forth in a member selected from the group consisting of SEQ ID NOs: 1-13; e.g., comprising the amino acid sequence:

```
                                                    (SEQ ID NO: 20)
MKVSAALLCLLLIAATFIPQGLAQPDAINAPVTCCYNFTNRKISVQRLASYRRITSSKCPKEAVI

FKTIVAKEICADPKQKWVQDSMDHLDKQTQTPKT

GGEPKSS

DKTHTCPPCPAPELLGGPSVFLEPPKPKDTLMISRTPEVTCVVVAVSHEDPEVKFNWYVDGVEVH

NAKTKPREEQYNSTYRVVSVLTVLHQDWLNGKEYKCKVSNKALPAPIEKTISKAKGQPREPQVYT

LPPSRDELTKNQVSLTCLVKGFYPSDIAVEWESNGQPENNYKTTPPVLDSDGSFFLYSKLTVDKS

RWQQGNVFSCSVMHEALHNHYTQKSLSLSPGK;
``` or comprising the amino acid sequence:

```
                                                    (SEQ ID NO: 16)
QPDAINAPVT CCYNFTNRKI SVQRLASYRR ITSSKCPKEA VIFKTIVAKE ICADPKQKWV

QDSMDHLDKQ TQTPKTGGEPKSSD KTHTCPPCPA PELLGGPSVF LFPPKPKDTL MISRTPEVTC

VVVAVSHEDP EVKFNWYVDG VEVHNAKTKP REEQYNSTYR VVSVLTVLHQ DWLNGKEYKC

KVSNKALPAP IEKTISKAKG QPREPQVYTL PPSRDELTKN QVSLTCLVKG FYPSDIAVEW

ESNGQPENNY KTTPPVLDSD GSFFLYSKLT VDKSRWQQGN VFSCSVMHEA LHNHYTQKSL

SLSPGK.
```

The present invention also provides an isolated polynucleotide (e.g., a cDNA) encoding any of said polypeptides; an isolated vector comprising the polynucleotide; an isolated host cell comprising the polynucleotide or a vector comprising said polynucleotide; e.g., wherein the host cell is a bacterial cell or a fungal cell, such as *E. coli, Pichia* or a Chinese hamster ovary cell. Also provided are compositions, e.g., pharmaceutical compositions, comprising any of said polypeptides or polynucleotides, and a carrier or buffer, e.g., a pharmaceutically acceptable carrier. Compositions comprising any of said polypeptides in association with one or more further therapeutic agents or a pharmaceutical composition thereof are also encompassed by the present invention; e.g., wherein the further therapeutic agent is a member selected from the group consisting of aspirin, diclofenac, diflunisal, etodolac, fenoprofen, floctafenine, flurbiprofen, ibuprofen, indomethacin, ketoprofen, ketorolac, meclofenamate, mefenamic acid, meloxicam, nabumetone, naproxen, oxaprozin, phenylbutazone, piroxicam, salsalate, sulindac, tenoxicam, tiaprofenic acid, tolmetin, betamethasone benzoate, betamethasone valerate, clobetasol propionate, desoximetasone, fluocinolone acetonide, flurandrenolide, a topical steroid, alclometasone dipropionate, aloe vera, amcinonide, amcinonide, anthralin, betamethasone dipropionate, betamethasone valerate, calcipotriene, clobetasol propionate, coal tar, Dead Sea salts, desonide, desonide; betamethasone valerate, desoximetasone, diflorasone diacetate, epsom salts, fluocinolone acetonide, fluocinonide, flurandrenolide, fluticasone propionate, halcinonide, halobetasol propionate, hydrocortisone valerate, hydrocortisone, mometasone furoate, oilated oatmeal, petroleum jelly, prednicarbate, salicylic acid, tazarotene, triamcinolone acetonide, a mixture of hydrocortisone, dexamethasone, methylprednisolone and prednisolone, alefacept, etanercept, cyclosporine, methotrexate, acitretin, isotretinoin, hydroxyurea, mycophenolate mofetil, sulfasalazine, 6-Thioguanine, anakinra, injectable gold, penicillamine, azathioprine, chloroquine, hydroxychloroquine, sulfasalazine, oral gold, auranofin, gold sodium thiomalate, aurothioglucose, mesalamine, sulfasalazine, budesonide, metronidazole, ciprofloxacin, azathioprine, 6-mercaptopurine or dietary supplementation of calcium, folate, vitamin B12, celecoxib, rofecoxib, valdecoxib, lumiracoxib, etoricoxib, efalizumab, adalimumab, infliximab and ABX-IL8.

The present invention also provides a method for making any of said polypeptides comprising transforming a host cell with an expression vector comprising a polynucleotide encoding said polypeptide under conditions suitable for said expression and, optionally, purifying the polypeptide.

In addition, the present invention provides a method for treating or preventing a medical disorder which is:
an inflammatory medical disorder,
obesity-associated insulin resistance,
Type 2 diabetes and diabetes-associated nephritis,
liver steatosis,
multiple sclerosis,
rheumatoid arthritis,
psoriasis,
colitis,
pancreatitis,
parasitic infection,
bacterial infection,
viral infection,
cancer; or
a cardiovascular or circulatory disorder including but not limited to atherosclerosis; in a subject (e.g., a human), comprising administering, to the subject, any of said polypeptides or a pharmaceutical composition thereof optionally in association with a further therapeutic agent or procedure (e.g., denosumab, aspirin, diclofenac, diflunisal, etodolac, fenoprofen, floctafenine, flurbiprofen, ibuprofen, indomethacin, ketoprofen, ketorolac, meclofenamate, mefenamic acid, meloxicam, nabumetone, naproxen, oxaprozin, phenylbutazone, piroxicam, salsalate, sulindac, tenoxicam, tiaprofenic acid, tolmetin, betamethasone benzoate, betamethasone valerate, clobetasol propionate, desoximetasone, fluocinolone acetonide, flurandrenolide, a topical steroid, alclometasone dipropionate, aloe vera, amcinonide, amcinonide, anthralin, betamethasone dipropionate, betamethasone valerate, calcipotriene, clobetasol propionate, coal tar, Dead Sea salts, desonide, desonide; betamethasone valerate, desoximetasone, diflorasone diacetate, epsom salts, fluocinolone acetonide, fluocinonide, flurandrenolide, fluticasone propionate, halcinonide, halobetasol propionate, hydrocortisone valerate, hydrocortisone, mometasone furoate, oilated oatmeal, petroleum jelly, prednicarbate, salicylic acid, tazarotene, triamcinolone acetonide, a mixture of hydrocortisone, dexamethasone, methylprednisolone and prednisolone, alefacept, etanercept, cyclosporine, methotrexate, acitretin, isotretinoin, hydroxyurea, mycophenolate mofetil, sulfasalazine, 6-Thioguanine, anakinra, injectable gold, penicillamine, azathioprine, chloroquine, hydroxychloroquine, sulfasalazine, oral gold, auranofin, gold sodium thiomalate, aurothioglucose, mesalamine, sulfasalazine, budesonide, metronidazole, ciprofloxacin, azathioprine, 6-mercaptopurine or dietary supplementation of calcium, folate, vitamin B12, celecoxib, rofecoxib, valdecoxib, lumiracoxib, etoricoxib, efalizumab, adalimumab, infliximab, ABX-IL8 or phototherapy); e.g., wherein the medical disorder is a member selected from the group consisting of appendicitis, peptic ulcer, gastric ulcer and duodenal ulcer, peritonitis, liver steatosis, pancreatitis, inflammatory bowel disease, colitis, ulcerative colitis, pseudomembranous colitis, acute colitis, ischemic colitis, diverticulitis, epiglottitis, achalasia, cholangitis, cholecystitis, coeliac disease, hepatitis, Crohn's disease, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, and urethritis, bronchitis, emphysema, rhinitis, fibrosis, cystic fibrosis, pneumonitis, adult respiratory distress syndrome, pneumoultramicroscopicsilicovolcanoconiosis, alvealitis, bronchiolitis, pharyngitis, pleurisy, sinusitis, dermatitis, atopic dermatitis, dermatomyositis, sunburn, urticaria warts, wheals, stenosis, restenosis, vasulitis, angiitis, endocarditis, arteritis, atherosclerosis, thrombophlebitis, pericarditis, myocarditis, myocardial ischemia, periarteritis nodosa, rheumatic fever, meningitis, encephalitis, multiple sclerosis, neuritis, neuralgia, uveitis, arthritides and arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcets's syndrome, allograft rejection and graft-versus-host disease.

DETAILED DESCRIPTION OF THE INVENTION

The present invention encompasses MCP1-Ig fusions that bear similarity to those set forth in US2007/0036750A1 but which exhibit surprising and unexpectedly improved activity. Surprisingly, the MCP1-Ig fusions of the invention have been demonstrated to exhibit comparable activity as compared to native MCP1 in vitro. It was determined that, at least in part, the ability to restore full MCP1 agonist/chemotactic activity depended on the presence of a specific peptide linker between MCP1 and the immunoglobulin (GGEPKSS (SEQ ID NO: 12)). Accordingly, MCP1-Ig fusions comprising this linker forms part of the present invention along with methods for treating various medical disorders.

For example, in a specific embodiment of the invention, the MCP1-Ig fusion protein of the present invention comprises the following amino acid sequence:

(SEQ ID NO: 16)
QPDAINAPVT CCYNFTNRKI SVQRLASYRR ITSSKCPKEA VIFKTIVAKE ICADPKQKWV

QDSMDHLDKQ TQTPKTGGEPKSSD KTHTCPPCPA PELLGGPSVF LFPPKPKDTL MISRTPEVTC

VVVAVSHEDP EVKFNWYVDG VEVHNAKTKP REEQYNSTYR VVSVLTVLHQ DWLNGKEYKC

KVSNKALPAP IEKTISKAKG QPREPQVYTL PPSRDELTKN QVSLTCLVKG FYPSDIAVEW

ESNGQPENNY KTTPPVLDSD GSFFLYSKLT VDKSRWQQGN VFSCSVMHEA LHNHYTQKSL

SLSPGK;
or,
(SEQ ID NO: 20)
MKVSAALLCLLLIAATFIPQGLAQPDAINAPVTCCYNFTNRKISVQRLASYRRITSSKCPKEAVI

FKTIVAKEICADPKQKWVQDSMDHLDKQTQTPKT

GGEPKSS

DKTHTCPPCPAPELLGGPSVFLFPPKPKDTLMISRTPEVTCVVVAVSHEDPEVKFNWYVDGVEVH

NAKTKPREEQYNSTYRVVSVLTVLHQDWLNGKEYKCKVSNKALPAPIEKTISKAKGQPREPQVYT

LPPSRDELTKNQVSLTCLVKGFYPSDIAVEWESNGQPENNYKTTPPVLDSDGSFFLYSKLTVDKS

RWQQGNVFSCSVMHEALHNHYTQKSLSLSPGK.

Molecular Biology

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook, et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984); F. M. Ausubel, et al. (eds.), *Current Protocols in Molecular Biology*, John Wiley & Sons, Inc. (1994).

"cDNA" comprises the open reading frame of a gene excluding introns and non-coding regulatory sequences.

A "polynucleotide", "nucleic acid" or "nucleic acid molecule" includes single or double stranded DNA; or single or double stranded RNA.

A "polynucleotide sequence", "nucleic acid sequence" or "nucleotide sequence" is a series of nucleotide bases (also called "nucleotides") in a nucleic acid, such as DNA or RNA, and means any chain of two or more nucleotides.

A "protein sequence", "peptide sequence" or "polypeptide sequence" or "amino acid sequence" includes a series of two or more amino acids in a protein, peptide or polypeptide.

The terms "isolated polynucleotide" or "isolated polypeptide" include a polynucleotide (e.g., RNA or DNA molecule, or a mixed polymer) or a polypeptide, respectively, which are partially or fully purified, e.g., separated from other components that are normally found in cells or in recombinant DNA expression systems. These components include, but are not limited to, cell membranes, cell walls, ribosomes, polymerases, serum components and extraneous genomic sequences.

An isolated polynucleotide or polypeptide will, preferably, be an essentially homogeneous composition of molecules but may contain some heterogeneity. In an embodiment of the invention, an isolated polynucleotide or polypeptide or cDNA is at a concentration of about 50 micrograms/ml to about 2000 micrograms/ml (e.g., 100, 500, 1000, 1200, 1500) or more, for example, in a vessel such as a plastic tube.

The term "host cell" includes any cell of any organism that is selected, modified, transfected, transformed, grown, or used or manipulated in any way, for the production of a substance by the cell, for example the expression or replication, by the cell, of a gene, a DNA or RNA sequence or a protein. Host cells include bacterial cells (e.g., *E. coli*) Although *E. coli* host cells are commonly used for bacterial expression of polypeptides, other bacteria, such as various strains of *Pseudomonas* and *Bacillus* (*B. subtilis*), are known in the art and can be used as well. Eukaryotic host cells include fungal cells such as those in the Saccharomycetaceae family, including Arxiozyma; Ascobotryozyma; Citeromyces; Debaryomyces; Dekkera; Eremothecium; lssatchenkia; Kazachstania; *Kluyveromyces*; Kodamaea; Lodderomyces; Pachysolen; *Pichia* (e.g., *Pichia pastoris, Pichia methanolica,* and *Hansenula polymorpha* (*Pichia angusta*); *Saccharomyces* (e.g., *S. cerevisiae*); Saturnispora; Tetrapisispora; Torulaspora; Williopsis; and *Zygosaccharomyces*. Higher eukaryotes include established tissue culture cell lines from animal, e.g., mammalian, cells (e.g., Chinese hamster ovary (CHO) cells; HEK293 cells, myeloma cells including but not limited to SP2/0, NS1, and NS0, murine macrophage J774 cells, and Caco2 cells.), or from non-mammalian origin, e.g., insect cells, and birds.

The nucleotide sequence of a polynucleotide may be determined by any method known in the art (e.g., chemical sequencing or enzymatic sequencing). "Chemical sequencing" of DNA includes methods such as that of Maxam and Gilbert (1977) (Proc. Natl. Acad. Sci. USA 74:560), in which DNA is randomly cleaved using individual base-specific reactions. "Enzymatic sequencing" of DNA includes methods such as that of Sanger (Sanger, et al., (1977) Proc. Natl. Acad. Sci. USA 74:5463).

The polynucleotides herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like.

In general, a "promoter" or "promoter sequence" is a DNA regulatory region capable of binding an RNA polymerase in a cell (e.g., directly or through other promoter-bound proteins or substances) and initiating transcription of a coding sequence. A promoter sequence is, in general, bounded at its 3' terminus by the transcription initiation site and extends upstream (5' direction) to include the minimum number of bases or elements necessary to initiate transcription at any level. Within the promoter sequence may be found a transcription initiation site (conveniently defined, for example, by mapping with nuclease S1), as well as protein binding domains (consensus sequences) responsible for the binding of RNA polymerase. The promoter may be operably associated with other expression control sequences, including enhancer and repressor sequences or with a polynucleotide of the invention. Promoters which may be used to control gene expression include, but are not limited to, T7 promoter (e.g., which is specific to only T7 RNA polymerase (not bacterial RNA polymerase)), cytomegalovirus (CMV) promoter (U.S. Pat. Nos. 5,385,839 and 5,168,062), the SV40 early promoter region (Benoist, et al., (1981) Nature 290:304-310), the promoter contained in the 3' long terminal repeat of Rous sarcoma virus (Yamamoto, et al., (1980) Cell 22:787-797), the herpes thymidine kinase promoter (Wagner, et al., (1981) Proc. Natl. Acad. Sci. USA 78:1441-1445), the regulatory sequences of the metallothionein gene (Brinster, et al., (1982) Nature 296:39-42); prokaryotic expression vectors such as the β-lactamase promoter (VIIIa-Komaroff, et al., (1978) Proc. Natl. Acad. Sci. USA 75:3727-3731), or the tac promoter (DeBoer, et al., (1983) Proc. Natl. Acad. Sci. USA 80:21-25); see also "Useful proteins from recombinant bacteria" in Scientific American (1980) 242:74-94; and promoter elements from yeast or other fungi such as the Gal 4 promoter, the ADC (alcohol dehydrogenase) promoter, PGK (phosphoglycerol kinase) promoter or the alkaline phosphatase promoter.

A coding sequence is "under the control of", "functionally associated with" or "operably associated with" transcriptional and translational control sequences when the sequences direct RNA polymerase mediated transcription of the coding sequence into RNA, preferably mRNA, which then may be RNA spliced (if it contains introns) and, optionally, translated into a protein encoded by the coding sequence.

The terms "express" and "expression" mean allowing or causing the information in a gene, RNA or DNA sequence to become manifest; for example, producing a protein by activating the cellular functions involved in transcription and translation of a corresponding gene. A DNA sequence is expressed in or by a cell to form an "expression product" such as an RNA (e.g., mRNA) or a protein. The expression product itself may also be said to be "expressed" by the cell.

The term "transformation" means the introduction of polynucleotide into a cell. A host cell that receives the introduced DNA or RNA has been "transformed" and is a "transformant". The DNA or RNA introduced to a host cell can come from any source, including cells of the same genus or species as the host cell, or from cells of a different genus or species.

The term "vector" includes a vehicle (e.g., a plasmid) by which a DNA or RNA sequence can be introduced into a host cell, so as to transform the host and, optionally, promote expression and/or replication of the introduced sequence.

Vectors that can be used in this invention include plasmids, viruses, bacteriophage, integratable DNA fragments, and other vehicles that may facilitate introduction of the polynucleotide into the host. Plasmids are the most commonly used form of vector but all other forms of vectors which serve a similar function and which are, or become, known in the art may be used. See, e.g., Pouwels, et al., *Cloning Vectors: A Laboratory Manual*, 1985 and Supplements, Elsevier, N.Y., and Rodriguez et al. (eds.), *Vectors: A Survey of Molecular Cloning Vectors and Their Uses*, 1988, Buttersworth, Boston, Mass.

The present invention comprises a method for producing MCP1-Ig fusions. In an embodiment of the invention, a polynucleotide encoding the fusion is inserted into an expression vector which is introduced into a suitable host cell (e.g., a bacterial cell, a fungal cell such as a *Pichia* cell including *Pichia pastoris*, or a eukaryotic cell such as a CHO cell). The polynucleotide may be chromosomally integrated into the host cell chromosomal DNA or ectopic and may exist in 1 or more copies per cell, e.g., 2, 5, 10, 20. The protein is then allowed to express in the host cell. The protein may then be optionally isolated from the host cell an/or host cell growth medium; and, optionally purified further. If the polypeptide is secreted from the host cell, the protein can be optionally purified from the cells and, optionally, purified further, e.g., from cell culture/growth medium. Any polypeptide described herein produced by such a method is also within the scope of the present invention.

The term "expression system" means a host cell and compatible vector which, under suitable conditions, can express a protein or nucleic acid which is carried by the vector and introduced to the host cell. Common expression systems include *Pichia* (e.g., *P. pastoris*) or *E. coli* host cells or mammalian host cells (e.g., CHO cells, HEK293 cells, and myeloma cells) and plasmid vectors, insect host cells and Baculovirus vectors, and mammalian host cells and vectors. The present invention includes methods for expressing an MCP1-Ig fusion using a suitable expression system; as well as expression systems comprising a vector comprising a polynucleotide encoding MCP1-Ig and/or a host cell comprising MCP1-Ig.

Expression of nucleic acids encoding MCP1-Ig can be carried out by conventional methods in either prokaryotic or eukaryotic cells. Prokaryotic host-vector systems include a wide variety of vectors for many different species. A representative vector for amplifying DNA is pBR322 or any of many of its derivatives (e.g., pUC18 or 19). Vectors that can be used to express the MCP1-Ig fusion include, but are not limited to, those containing the lac promoter (pUC-series); trp promoter (pBR322-trp); lpp promoter (the pIN-series); lambda-pP or pR promoters (pOTS); or hybrid promoters such as ptac (pDR540). See Brosius et al., "Expression Vectors Employing Lambda-, trp-, lac-, and lpp-derived Promoters", in Rodriguez and Denhardt (eds.) *Vectors: A Survey of Molecular Cloning Vectors and Their Uses*, 1988, Buttersworth, Boston, pp. 205-236. Many polypeptides can be expressed, at high levels, in an *E. coli*/T7 expression system as disclosed in U.S. Pat. Nos. 4,952,496, 5,693,489 and 5,869,320 and in Davanloo, P., et al., (1984) Proc. Natl. Acad. Sci. USA 81: 2035-2039; Studier, F. W., et al., (1986) J. Mol. Biol. 189: 113-130; Rosenberg, A. H., et al., (1987) Gene 56: 125-135; and Dunn, J. J., et al., (1988) Gene 68: 259.

The T7 expression system comprises pET plasmids which contain an expression cassette in which the gene of interest (e.g., MCP1-Ig fusion) is inserted behind an extremely strong T7 promoter from the *E. coli* bacteriophage T7 (Studier et al., J. Mol. Biol. 189(1):113-30 (1986)) which is activated by T7 RNA polymerase but not the *E. coli* host cell RNA polymerase. In the absence of the T7 RNA polymerase, this promoter is shut off. For expression to occur, the pET plasmids are transformed into bacteria strains that typically contain a single copy of the T7 RNA polymerase on the chromosome in a lambda lysogen (the most commonly used lysogen is known as DE3). The T7 RNA polymerase is under the control of the Lac-UV5 lac promoter. When cells are grown in media without lactose, the lac repressor (lacI) binds to the lac operator and prevents transcription from the lac promoter. When lactose is the sole carbon source, or when the lactose analog, e.g., isopropyl-beta-D-thiogalactopyranoside (IPTG), is added to the media, lactose (or IPTG) binds to the repressor and induces its dissociation from the operator, permitting transcription of T7 RNA polymerase from the promoter. T7 RNA polymerase causes expression of the gene operably associated with the T7 promoter. Addition of glucose to the culture media contributes to repression of the T7 RNA polymerase via the mechanism of catabolite repression.

Higher eukaryotic tissue culture cells may also be used for the recombinant production of the MCP1-Ig fusion of the invention. Higher eukaryotic tissue culture cell lines can be used, including insect baculovirus expression systems and mammalian cells. Transformation or transfection and propagation of such cells have become a routine procedure. Examples of useful cell lines include HeLa cells, Chinese hamster ovary (CHO) cell lines, HEK 293 cells, myeloma cells, J774 cells, Caco2 cells, baby rat kidney (BRK) cell lines, insect cell lines, bird cell lines, and monkey (COS) cell lines. Typically, expression vectors for such cell lines include an origin of replication, a promoter, a translation initiation site, RNA splice sites (if genomic DNA is used), a polyadenylation site, and a transcription termination site. These vectors also, usually, contain a selection gene or amplification gene. Suitable expression vectors may be plasmids, viruses, or retroviruses carrying promoters derived, e.g., from such sources as adenovirus, SV40, parvoviruses, vaccinia virus, or cytomegalovirus. Examples of expression vectors include pCR®3.1, pcDNA1, pCD (Okayama, et al., (1985) Mol. Cell. Biol. 5:1136), pMC1neo Poly-A (Thomas, et al., (1987) Cell 51:503), pREP8, pSVSPORT and derivatives thereof, and baculovirus vectors such as pAC373 or pAC610.

In an embodiment of the invention, the MCP1-Ig fusion can be purified by protein A or protein G chromatography. Protein A and protein G bind preferentially to immunoglobulins. Furthermore, the polypeptide can be purified by standard methods, including, but not limited to, salt or alcohol precipitation, affinity chromatography, preparative disc-gel electrophoresis, isoelectric focusing, high pressure liquid chromatography (HPLC), reversed-phase HPLC, gel filtration, cation exchange, anion exchange, partition chromatography, and/or countercurrent distribution. Such purification methods are well known in the art and are disclosed, e.g., in "Guide to Protein Purification", Methods in Enzymology, Vol. 182, M. Deutscher, Ed., 1990, Academic Press, New York, N.Y. Where a polypeptide is being isolated from a cellular or tissue source, it is preferable to include one or more inhibitors of proteolytic enzymes in the assay system, such as phenylmethanesulfonyl fluoride (PMSF), Pefabloc SC, pepstatin, leupeptin, chymostatin and EDTA.

Modifications (e.g., post-translational modifications) that occur in a polypeptide often will be a function of how it is made. For polypeptides made by expressing a cloned gene in a host, for instance, the nature and extent of the modifications, in large part, will be determined by the host cell's post-translational modification capacity and the modification signals present in the polypeptide amino acid sequence. For instance, as is well known, glycosylation often does not occur in bacterial hosts such as *E. coli*. Accordingly, when glycosylation of the MCP1-Ig fusion is desired, the polypeptide can be expressed in a glycosylating host, generally a eukaryotic cell (e.g., an insect cell such as *Spodoptera fruigiperda* (Sf9 or Sf21) or *Trichoplusia ni* (High 5)). If desired, deglycosylation enzymes can be used to remove carbohydrates attached during production in eukaryotic expression systems.

Pegylation or addition of polyethylene glycol (PEG) to a polypeptide such as the MCP1-Ig fusion can be accomplished using conventional and well known methods in the art (see e.g., U.S. Pat. No. 5,691,154; U.S. Pat. No. 5,686,071; U.S. Pat. No. 5,639,633; U.S. Pat. No. 5,492,821; U.S. Pat. No. 5,447,722; U.S. Pat. No. 5,091,176).

MCP1-Ig Fusion

The present invention encompasses MCP1-Ig fusion polypeptides set forth herein. The fusions comprise MCP1 (e.g., human MCP1) unprocessed or a mature fragment thereof (i.e., lacking the signal sequence) linked to an immunoglobulin such as the gamma-1 variant polypeptide via a peptide linker comprising or consisting of the amino acid sequence set forth in SEQ ID NO: 1, 2, 3, 4, 5, 6, 7, 8, 9, 10, 11, 12 or 13.

MCP1 Unprocessed

```
                                              (SEQ ID NO: 14)
MKVSAALLCLLLIAATFIPQGLAQPDAINAPVTCCYNFTNRKISVQRLAS

YRRITSSKCPKEAVIFKTIVAKEICADPKQKWVQDSMDHLDKQTQTPKT
```

MCP1 Mature Fragment

```
                                              (SEQ ID NO: 17)
QPDAINAPVTCCYNFTNRKISVQRLASYRRITSSKCPKEAVIFKTIVAK

EICADPKQKWVQDSMDHLDKQTQ
```

Linkers

| | | |
|---|---|---|
| VEPKSC | (LPD1375) | (SEQ ID NO: 1) |
| GSVEPKSC | (LPD1388) | (SEQ ID NO: 2) |
| GSEPKSC | (LPD1389) | (SEQ ID NO: 3) |
| GSGEPKSC | (LPD1390) | (SEQ ID NO: 4) |
| GSGSEPKSC | (LPD1391) | (SEQ ID NO: 5) |
| GGEPKSC | (LPD1393) | (SEQ ID NO: 6) |
| GGGEPKSC | (LPD1394) | (SEQ ID NO: 7) |
| GSVEPKSS | (LPD1417) | (SEQ ID NO: 8) |
| GSEPKSS | (LPD1418) | (SEQ ID NO: 9) |
| GSGEPKSS | (LPD1419) | (SEQ ID NO: 10) |
| GSGSEPKSS | (LPD1420) | (SEQ ID NO: 11) |
| GGEPKSS | (LPD1421) | (SEQ ID NO: 12) |
| GGGEPKSS | (LPD1422) | (SEQ ID NO: 13) |

IMMUNOGLOBULIN GAMMA-1 VARIANT with an aspartic acid residue at canonical position 265 substituted with an alanine residue to eliminate Fc receptor binding capability. (Clynes et al. Nature 2000 6(4):443-6)

(SEQ ID NO: 15)
DKTHTCPPCPAPELLGGPSVFLFPPKPKDTLMISRTPEVTCVVVAVSHEDPEVKFNWYVDGVEVH

NAKTKPREEQYNSTYRVVSVLTVLHQDWLNGKEYKCKVSNKALPAPIEKTISKAKGQPREPQVYT

LPPSRDELTKNQVSLTCLVKGFYPSDIAVEWESNGQPENNYKTTPPVLDSDGSFFLYSKLTVDKS

RWQQGNVFSCSVMHEALHNHYTQKSLSLSPGK

MCP1-Ig fusions comprising mature human MCP1 and the IgG1 variant linked by the linker of SEQ ID NO: 1 may be referred to herein as LPD1375;
MCP1-Ig fusions comprising mature human MCP1 and the IgG1 variant linked by the linker of SEQ ID NO: 2 may be referred to herein as LPD1388;
MCP1-Ig fusions comprising mature human MCP1 and the IgG1 variant linked by the linker of SEQ ID NO: 3 may be referred to herein as LPD1389;
MCP1-Ig fusions comprising mature human MCP1 and the IgG1 variant linked by the linker of SEQ ID NO: 4 may be referred to herein as LPD1390;
MCP1-Ig fusions comprising mature human MCP1 and the IgG1 variant linked by the linker of SEQ ID NO: 5 may be referred to herein as LPD1391;
MCP1-Ig fusions comprising mature human MCP1 and the IgG1 c variant linked by the linker of SEQ ID NO: 6 may be referred to herein as LPD1393;
MCP1-Ig fusions comprising mature human MCP1 and the IgG1 variant linked by the linker of SEQ ID NO: 7 may be referred to herein as LPD1394;
MCP1-Ig fusions comprising mature human MCP1 and the IgG1 variant linked by the linker of SEQ ID NO: 8 may be referred to herein as LPD1417;
MCP1-Ig fusions comprising mature human MCP1 and the IgG1 variant linked by the linker of SEQ ID NO: 9 may be referred to herein as LPD1418;
MCP1-Ig fusions comprising mature human MCP1 and the IgG1 variant linked by the linker of SEQ ID NO: 10 may be referred to herein as LPD1419;
MCP1-Ig fusions comprising mature human MCP1 and the IgG1 variant linked by the linker of SEQ ID NO: 11 may be referred to herein as LPD1420;
MCP1-Ig fusions comprising mature human MCP1 and the IgG1 variant linked by the linker of SEQ ID NO: 12 may be referred to herein as LPD1421; and
MCP1-Ig fusions comprising mature human MCP1 and the IgG1 variant linked by the linker of SEQ ID NO: 13 may be referred to herein as LPD1422.

Therapeutic Compositions and Methods

The present invention includes methods for treating or preventing any medical condition or disorder or disease that is treatable by administering a therapeutically effective amount of MCP1-Ig fusion of the invention (e.g., LPD1421) optionally in association with a therapeutically effective amount of a further therapeutic agent, by decreasing MCP-1 mediated migration of MCP1 receptor-bearing cells (e.g., CCR2-bearing cells; such as monocytes, dendritic cells, macrophages or memory T lymphocytes) into inflamed tissues, and by promoting the egress of MCP1 receptor-bearing cells from inflamed tissues. The MCP1-Ig fusion can be administered, in an embodiment of the invention, for a prolonged period of time so as to reach circulating levels sufficient to keep the receptor-bearing cells in the circulation in a desensitization state and therefore unresponsive to the endogenous MCP1 released by the inflamed tissues. The circulating MCP1-Ig fusion can also form a gradient toward the inflamed tissues to attract the MCP1 receptor-bearing cells already infiltrated to leave the tissues. Furthermore, the anti-inflammatory effect can be enhanced by the capability of MCP1-Ig fusion to re-program the immune system toward the anti-inflammatory pathway. Compared to small-molecule CCR2 antagonists which only block monocyte trafficking into the inflamed tissues, MCP-Ig is apparently superior due to the additional capability of promoting macrophage egress and steering the immune system away from the pro-inflammatory pathway.

A pharmaceutical composition of the invention may be prepared by any methods well known in the art of pharmacy; see, e.g., Gilman, et al., (eds.) (1990), *The Pharmacological Bases of Therapeutics,* 8th Ed., Pergamon Press; A. Gennaro (ed.), *Remington's Pharmaceutical Sciences,* 18th Edition, (1990), Mack Publishing Co., Easton, Pa.; Avis, et al., (eds.) (1993) *Pharmaceutical Dosage Forms: Parenteral Medications* Dekker, New York; Lieberman, et al., (eds.) (1990) *Pharmaceutical Dosage Forms: Tablets* Dekker, New York; and Lieberman, et al., (eds.) (1990), *Pharmaceutical Dosage Forms: Disperse Systems* Dekker, New York.

The present invention further includes methods for treating or preventing an inflammatory disorder or medical inflammatory disorder, in a subject, by administering a therapeutically effective amount of MCP-1 fusion (e.g., LPD1421) to the subject or a pharmaceutical composition thereof (e.g., comprising a pharmaceutically acceptable carrier) optionally in association with a therapeutically effective amount of a further therapeutic agent or therapeutic procedure. The term "inflammatory disorder" or "medical inflammatory disorder" includes, in an embodiment of the invention, psoriasis (e.g., nail psoriasis, scalp psoriasis, plaque psoriasis, pustular psoriasis, guttate psoriasis, inverse psoriasis, erythrodermic or psoriatic arthritis), ankylosing spondylitis, appendicitis, peptic ulcer, gastric ulcer and duodenal ulcer, peritonitis, liver steatosis, pancreatitis, inflammatory bowel disease, colitis, ulcerative colitis, pseudomembranous colitis, acute colitis, ischemic colitis, diverticulitis, epiglottitis, achalasia, cholangitis, cholecystitis, coeliac disease, hepatitis, Crohn's disease (e.g., ileocolitis, ileitis, gastroduodenal Crohn's disease, jejunoileitis or Crohn's (granulomatous) colitis), enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, and urethritis, bronchitis, emphysema, rhinitis, cystic fibrosis, pneumonitis, adult respiratory distress syndrome, pneumoultramicroscopicsilicovolcanoconiosis, alvealitis, bronchiolitis, pharyngitis, pleurisy, sinusitis, dermatitis, atopic dermatitis, dermatomyositis, sunburn, urticaria warts, wheals, stenosis, restenosis, vasulitis, angiitis, endocarditis, arteritis, atherosclerosis, thrombophlebitis, pericarditis, myocarditis, myocardial ischemia, periarteritis nodosa, rheumatic fever, meningitis, encephalitis, multiple sclerosis, neuritis, neuralgia, uveitis (e.g., anterior, posterior, intermediate or diffuse), arthritides and arthralgias, osteomyelitis, fasciitis, Paget's disease, gout, periodontal disease, rheumatoid arthritis (e.g., polyarticular-course juvenile rheumatoid arthritis or psoriatic arthritis), synovitis, myasthenia gravis, thryoiditis, systemic lupus erythematosus, Goodpasture's syndrome, Behcets's syndrome, allograft rejection or graft-versus-host disease.

An embodiment of the invention the present invention includes methods for treating or preventing one or more disorders selected from the group consisting of psoriasis, ankylosing spondylitis, inflammatory bowel disease, colitis, ulcerative colitis, acute colitis, coeliac disease, anaphylactic shock, immune complex disease, dermatitis, atopic dermatitis, liver steatosis, pancreatitis, Crohn's disease, enteritis, cystic fibrosis, multiple sclerosis, neuritis, neuralgia, uveitis, arthritides, arthralgia, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcets syndrome, allograft rejection, graft-versus-host disease, granulomatosis, sarcoidosis, endocarditis, arteritis, atherosclerosis, myocarditis, sepsis, septicemia, endotoxic shock, reperfusion injury and organ ischemia, in a subject, by administering a therapeutically effective amount of MCP-1 fusion (e.g., LPD1421) to the subject or a pharmaceutical composition thereof (e.g., comprising a pharmaceutically acceptable carrier) optionally in association with a therapeutically effective amount of a further therapeutic agent or therapeutic procedure.

The present invention further includes methods for treating or preventing obesity-related insulin resistance, in a subject, by administering a therapeutically effective amount of MCP-1 fusion (e.g., LPD1421) to the subject or a pharmaceutical composition thereof (e.g., comprising a pharmaceutically acceptable carrier) optionally in association with a therapeutically effective amount of a further therapeutic agent or therapeutic procedure. An abundance of MCP-1 in both white adipose tissue and plasma is increased in obese mice, suggesting that MCP-1 might also be an adipokine whose expression is increased in obesity. Furthermore, insulin resistance in adipose tissue induced in mice by a high-fat diet, is reduced extensively in homozygous mcp1 knock-outs compared with wild-type animals (Kanda et al., J Clin Invest. 2006 116(6): 1494-1505).

The present invention also includes a method for treating or preventing a parasitic, viral or bacterial infection in a subject by administering, to the subject, a therapeutically effective amount of MCP1-Ig fusion (e.g., LPD1421) or a pharmaceutical composition thereof (e.g., comprising a pharmaceutically acceptable carrier) optionally in association with a therapeutically effective amount of a further therapeutic agent or therapeutic procedure. In an embodiment of the invention, the infection is herpes simplex virus infection (e.g., HSV1 or HSV2), human T lymphotropic virus (HTLV; e.g., type I) infection, HIV infection, HIV neuropathy, meningitis, hepatitis (A, B or C, or the like), septic arthritis, peritonitis, pneumonia, epiglottitis, *E. coli* 0157:h7, hemolytic uremic syndrome, thrombolytic thrombocytopenic purpura, malaria, dengue hemorrhagic fever, leishmaniasis, leprosy, toxic shock syndrome, streptococcal myositis, gas gangrene, *mycobacterium tuberculosis, mycobacterium avium intracellulare, pneumocystis carinii* pneumonia, pelvic inflammatory disease, orchitis, epidydimitis, *legionella*, lyme disease, influenza a, epstein-barr virus, vital-associated hemaphagocytic syndrome, vital encephalitis or aseptic meningitis.

The present invention also includes a method for treating or preventing a cancer or malignancy (e.g., breast, ovarian, stomach, endometrial, salivary gland, lung, kidney, colon, colorectal, thyroid, pancreatic, prostate or bladder cancer) in a subject by administering, to the subject, a therapeutically effective amount of MCP1-Ig fusion (e.g., LPD1421) or a pharmaceutical composition thereof (e.g., comprising a pharmaceutically acceptable carrier) optionally in association with a therapeutically effective amount of a further therapeutic agent.

The present invention also includes a method for treating or preventing a any cardiovascular or circulatory disorder in a subject by administering, to the subject, a therapeutically effective amount of MCP1-Ig fusion (e.g., LPD1421) or a pharmaceutical composition thereof (e.g., comprising a pharmaceutically acceptable carrier) optionally in association with a therapeutically effective amount of a further therapeutic agent. In an embodiment of the invention, the disease or disorder is cardiac stun syndrome, myocardial infarction, congestive heart failure, stroke, ischemic stroke, hemorrhage, arteriosclerosis, atherosclerosis, restenosis, diabetic ateriosclerotic disease, hypertension, arterial hypertension, renovascular hypertension, syncope, shock, syphilis of the cardiovascular system, heart failure, cor pulmonale, primary pulmonary hypertension, cardiac arrhythmias, atrial ectopic beats, atrial flutter, atrial fibrillation (sustained or paroxysmal), post perfusion syndrome, cardiopulmonary bypass inflammation response, chaotic or multifocal atrial tachycardia, regular narrow QRS tachycardia, specific arrythmias, ventricular fibrillation, His bundle arrythmias, atrioventricular block, bundle branch block, myocardial ischemic disorders, coronary artery disease, angina pectoris, myocardial infarction, cardiomyopathy, dilated congestive cardiomyopathy, restrictive cardiomyopathy, valvular heart diseases, endocarditis, pericardial disease, cardiac tumors, aordic and peripheral aneuryisms, aortic dissection, inflammation of the aorta, occulsion of the abdominal aorta and its branches, peripheral vascular disorders, occulsive arterial disorders, peripheral atherlosclerotic disease, thromboangitis obliterans, functional peripheral arterial disorders, Raynaud's phenomenon and disease, acrocyanosis, erythromelalgia, venous diseases, venous thrombosis, varicose veins, arteriovenous fistula, lymphederma, lipedema, unstable angina, reperfusion injury, post pump syndrome or ischemia-reperfusion injury.

A pharmaceutical composition containing the MCP1-Ig fusion (e.g., LPD1421) can be prepared using conventional pharmaceutically acceptable excipients and additives and conventional techniques. Such pharmaceutically acceptable excipients and additives include non-toxic compatible fillers, binders, disintegrants, buffers, preservatives, anti-oxidants, lubricants, flavorings, thickeners, coloring agents, emulsifiers and the like.

All routes of administration are contemplated including, but not limited to, parenteral (e.g., subcutaneous, intravenous, intraperitoneal, intratumoral or intramuscular) and non-parenteral (e.g., oral, transdermal, intranasal, intraocular, sublingual, inhalation, rectal and topical).

Injectables can be prepared in conventional forms, either as liquid solutions or suspensions, solid forms suitable for solution or suspension in liquid prior to injection, or as emulsions. The injectables, solutions and emulsions can also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations are generally added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN-80). A sequestering or chelating agent of metal ions include EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

Preparations for parenteral administration can include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

Implantation of a slow-release or sustained-release system, such that a constant level of dosage is maintained is also contemplated herein. Briefly, in this embodiment, MCP1-Ig fusion (e.g., LPD1421) is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient diffuses through the outer polymeric membrane in a release rate controlling step. The percentage of active compound contained in such parenteral compositions is highly dependent on the specific nature thereof, as well as the activity of the MCP1-Ig fusion and the needs of the subject.

The concentration of the MCP1-Ig fusion can be adjusted so that an injection provides an effective amount to produce the desired pharmacological effect.

A unit-dose parenteral preparation comprising MCP1-Ig fusion can be packaged, e.g., in an ampoule, a vial or a syringe with a needle. All preparations for parenteral administration must be sterile, as is known and practiced in the art. Such a preparation forms part of the present invention.

An MCP1-Ig fusion can be formulated into a lyophilized powder, which can be reconstituted for administration as solutions, emulsions and other mixtures. The powder may also be reconstituted and formulated as a solid or gel.

Sterile, lyophilized powder can be prepared by dissolving MCP1-Ig fusion in a suitable solvent. Solvents (e.g., water), for formulation of an MCP-1 fusion, may contain an excipient which improves the stability or another pharmacological component. Excipients that may be used to formulation a fusion of the invention include, but are not limited to, sugars and polyols such as dextrose, sorbital, fructose, corn syrup, xylitol, glycerin, glucose, sucrose or another suitable agent. The solvent may contain a buffer, such as citrate, sodium or potassium phosphate or another such buffer known to those of skill in the art at, in one embodiment, about neutral pH. Sterile filtration of a pharmaceutical formulation containing a fusion of the invention is known to those of skill in the art. Each vial can contain a single dosage or multiple dosages of the MCP1-Ig fusion. A pharmaceutical formulation of the invention can be stored under appropriate conditions, such as at about 4° C. to room temperature.

Reconstitution of a lyophilized powder containing a MCP1-Ig fusion of the invention with water for injection provides a formulation for use in parenteral administration. For reconstitution, the lyophilized powder can be added to sterile water or another suitable carrier.

The scope of the present invention includes methods comprising administering an MCP1-Ig fusion or a pharmaceutical composition thereof, in association with, for example, one or more further therapeutic agents as well as compositions comprising MCP1-Ig fusion in association with a further therapeutic agent. In an embodiment of the invention, the other therapeutic agent is an agent that, when administered to a subject, treats or prevents a medical condition in the subject. The administration and dosage of any such agent is, when possible, according to the schedule listed in the product information sheet of the approved agents, in the *Physicians' Desk Reference* 2003 (*Physicians' Desk Reference,* 57th Ed); Medical Economics Company; ISBN: 1563634457; 57th edition (November 2002), as well as therapeutic protocols well known in the art.

The term "in association with" indicates that the MCP1-Ig fusion (e.g., LPD1421) and a further therapeutic agent can be formulated into a single composition for simultaneous delivery or formulated separately into two or more compositions (e.g., a kit). Furthermore, each component can be administered to a subject at a different time than when the other component is administered; for example, each administration may be given non-simultaneously (e.g., separately or sequentially) at several intervals over a given period of time. Moreover, the separate components may be administered to a subject by the same or by a different route (e.g., orally, intravenously, subcutaneously).

A "further therapeutic agent" or "further chemotherapeutic agent" is any agent, other than the MCP1-Ig, that, when administered to a subject, brings about a desired or beneficial therapeutic effect, such as prevention, elimination or reduction of the progression or severity of symptoms associated with a given medical condition (e.g., an inflammatory disorder). A further therapeutic agent may be, for example, an anti-inflammatory agent or a pain reliever. In an embodiment of the invention, the further therapeutic agent is a non-steroidal anti-inflammatory drug (NSAID), an immunosuppressive drug, a selective COX-2 inhibitor, a TNF inhibitor, or an inhibitor of an inflammatory cytokine. Inhibitors can be any type of molecule including, for example, a small organic molecule or an antibody or antigen-binding fragment of an antibody.

Further therapeutic agents that may be administered or combined in association with the MCP1-Ig fusion (e.g., LPD1421) include natalizumab. The present invention includes embodiments of the invention wherein an MCP1-Ig fusion is administered to a subject to treat multiple sclerosis in association with natalizumab (e.g., Tysabri).

Further therapeutic agents that may be administered or combined in association with the MCP1-Ig fusion (e.g., LPD1421) include one or more non-steroidal anti-inflammatory drug (NSAIDs) such as aspirin, diclofenac, diflunisal, etodolac, fenoprofen, floctafenine, flurbiprofen, ibuprofen, indomethacin, ketoprofen, ketorolac, meclofenamate, mefenamic acid, meloxicam, nabumetone, naproxen, oxaprozin, phenylbutazone, piroxicam, salsalate, sulindac, tenoxicam, tiaprofenic acid or tolmetin. For example, these NSAIDs may be administered with the fusion to treat any inflammatory disorder discussed herein (e.g., rheumatoid arthritis).

Further therapeutic agents that may be administered or combined in association with the MCP1-Ig fusion (e.g., LPD1421) include one or more topical medications, for example, anthralin, calcipotriene, salicylic acid, coal tar, tazarotene, topical steroids (e.g., Clobetasol propionate; Clobetasol propionate; Betamethasone dipropionate; Clobetasol propionate; Diflorasone diacetate; Clobetasol propionate Halobetasol propionate; Amcinonide; Betamethasone dipropionate; Betamethasone dipropionate; Mometasone furoate; Diflorasone diacetate; Halcinonide; Fluocinonide; Diflorasone diacetate; Betamethasone dipropionate; Diflorasone diacetate; Desoximetasone; Desoximetasone; Triamcinolone acetonide; Fluticasone propionate; Amcinonide; Betamethasone dipropionate; Diflorasone diacetate; Fluocinonide; Betamethasone valerate; Diflorasone diacetate; Betamethasone dipropionate; Desoximetasone; Betamethasone valerate; Triamcinolone acetonide; Flurandrenolide; Fluocinolone acetonide; Mometasone furoate; Triamcinolone acetonide; Fluocinolone acetonide; Betamethasone benzoate; Hydrocortisone valerate; Flurandrenolide; Fluticasone propionate; Prednicarbate; Desonide; Betamethasone dipropionate; Triamcinolone acetonide; Hydrocortisone; Fluocinolone acetonide; Betamethasone benzoate; Betamethasone valerate; Hydrocortisone valerate; Alclometasone dipropionate; Desonide; Fluocinolone acetonide; Desonide; Betamethasone valerate; or a mixture of hydrocortisone, dexamethasone, methylprednisolone and prednisolone), petroleum jelly, aloe vera, oilated oatmeal, epsom salts or Dead Sea salts. For example, these topical agents may be administered with the fusion to treat any skin disorder discussed herein (e.g., psoriasis).

Further therapeutic agents that may be administered or combined in association with the MCP1-Ig fusion (e.g., LPD1421) include one or more of alefacept, etanercept, cyclosporine, methotrexate, acitretin, isotretinoin, hydroxyurea, mycophenolate mofetil, sulfasalazine or 6-Thioguanine.

The present invention includes embodiments of the invention wherein an MCP1-Ig fusion (e.g., LPD1421) is administered to a subject, e.g., to treat rheumatoid arthritis, in association with methotrexate.

Further therapeutic agents that may be administered or combined in association with the MCP1-Ig fusion (e.g., LPD1421) include one or more of anakinra, abatacept, injectable gold, penicillamine, azathioprine, chloroquine, hydroxychloroquine, sulfasalazine or oral gold (e.g., auranofin, gold sodium thiomalate or aurothioglucose).

Further therapeutic agents that may be administered or combined in association with the MCP1-Ig fusion (e.g., LPD1421) include one or more of mesalamine, sulfasalazine, budesonide, metronidazole, ciprofloxacin, azathioprine, 6-mercaptopurine or dietary supplementation of calcium, folate or vitamin B12.

Further therapeutic agents that may be administered or combined in association with the MCP1-Ig fusion (e.g., LPD1421) include one or more selective COX2 inhibitors (that inhibit COX-2 selectively over that of COX-1) such as celecoxib (Celebrex®), rofecoxib (e.g., Vioxx), valdecoxib (e.g., Bextra), lumiracoxib (e.g., Prexige) or etoricoxib (e.g., Arcoxia). The present invention includes embodiments of the invention wherein an MCP1-Ig fusion is administered to a subject to treat rheumatoid arthritis in association with one or more selective COX2 inhibitors such as celecoxib (e.g., Celebrex), rofecoxib (e.g., Vioxx), valdecoxib (e.g., Bextra), lumiracoxib (e.g., Prexige) or etoricoxib (e.g., Arcoxia). For example, these selective COX2 inhibitors may be administered with the fusion to treat any inflammatory disorder discussed herein (e.g., rheumatoid arthritis).

Further therapeutic agents that may be administered or combined in association with the MCP1-Ig fusion (e.g., LPD1421) include one or more antibodies such as denosumab, efalizumab (e.g., Raptiva), adalimumab (e.g., Humira), infliximab (e.g., Remicade), rituximab (e.g., Rituxan), tocilizumab (e.g., Actemra), or ABX-IL8. The present invention includes embodiments of the invention wherein an MCP1-Ig fusion is administered to a subject to treat rheumatoid arthritis in association with one or more antibodies such as efalizumab (e.g., Raptiva), adalimumab (e.g., Humira), infliximab (e.g., Remicade), rituximab (e.g., rituxan), tocilizumab (e.g., actemra), or ABX-IL8.

Further therapeutic agents that may be administered or combined in association with the MCP1-Ig fusion (e.g., LPD1421) include a IL-23 inhibitor (e.g., p19 inhibitor), an IL-23 receptor inhibitor, an IL-6 inhibitor, an IL-6 receptor inhibitor, an IL-17 inhibitor (e.g., inhibitor of IL-17A, IL-17B, IL-17C, IL-17D, IL-17E (also called IL-25) or IL-17F), a RANKL inhibitor (e.g., denosumab) or a RANK inhibitor.

Further therapeutic agents that may be administered or combined in association with the MCP1-Ig fusion (e.g., LPD1421) include denosumab or an antigen-binding fragment thereof an isolated antibody or antigen-binding fragment thereof that comprises a heavy chain immunoglobulin that comprises the amino acid sequence:

```
                                                          (SEQ ID NO: 21)
  1 EVQLLESGGG LVQPGGSLRL SCAASGFTFS SYAMSWVRQA PGKGLEWVSG

51 ITGSGGSTYY ADSVKGRFTI SRDNSKNTLY LQMNSLRAED TAVYYCAKDP

101 GTTVIMSWFD PWGQGTLVTV SSASTKGPSV FPLAPCSRST SESTAALGCL

151 VKDYFPEPVT VSWNSGALTS GVHTFPAVLQ SSGLYSLSSV VTVPSSNFGT
```

```
201 QTYTCNVDHK PSNTKVDKTV ERKCCVECPP CPAPPVAGPS VFLFPPKPKD

251 TLMISRTPEV TCVVVDVSHE DPEVQFNWYV DGVEVHNAKT KPREEQFNST

301 FRVVSVLTVV HQDWLNGKEY KCKVSNKGLP APIEKTISKT KGQPREPQVY

351 TLPPSREEMT KNQVSLTCLV KGFYPSDIAV EWESNGQPEN NYKTTPPMLD

401 SDGSFFLYSK LTVDKSRWQQ GNVFSCSVMH EALHNHYTQK SLSLSPGK;
``` or that comprises the heavy chain CDRs of such a heavy chain; and/or a light chain immunoglobulin that comprises the amino acid sequence:

```
                                                    (SEQ ID NO: 22)
  1 EIVLTQSPGT LSLSPGERAT LSCRASQSVR GRYLAWYQQK PGQAPRLLIY

51 GASSRATGIP DRFSGSGSGT DFTLTISRLE PEDFAVFYCQ QYGSSPRTFG

101 QGTKVEIKRT VAAPSVFIFP PSDEQLKSGT ASVVCLLNNF YPREAKVQWK

151 VDNALQSGNS QESVTEQDSK DSTYSLSSTL TLSKADYEKH KVYACEVTHQ

201 GLSSPVTKSF NRGEC;
``` or that comprises the light chain CDRs of such a light chain.

In an embodiment of the invention, the MCP1-Ig fusion (e.g., LPD1421) is administered, to a subject, in association with phototherapy, particularly, wherein the subject suffers from psoriasis. In such an embodiment, the subject is exposed to sunlight, UVB light, PUVA (psoralen plus ultraviolet A). PUVA (psoralin-UVA) or laser light. PUVA uses ultraviolet A light to treat psoriasis in combination with psoralen, an oral or topical medication that makes your skin more sensitive to light. Lasers emit highly focused beams of light that affect primarily the psoriatic skin while healthy skin is not exposed significantly. One type of laser, the XTRAC excimer laser, uses highly focused ultraviolet B light. Another type of laser used for psoriasis is a pulsed dye laser, which uses pulses of yellow light—different from the ultraviolet rays used in UVB or XTRAC—to destroy some of the blood cells that grow in patches of psoriasis. Treatment with pulsed dye lasers usually takes a few months, with appointments every three weeks.

The term "subject" or "patient" refers to a mammal, such as a human.

Dosage and Administration

Typical protocols for the therapeutic administration of a composition of the invention are well known in the art. Pharmaceutical compositions of the invention may be administered, for example, by any parenteral (e.g., subcutaneous injection, intramuscular injection, intravenous injection) or non-parenteral route (e.g., orally, nasally).

Pills and capsules of the invention can be administered orally. Injectable compositions can be administered with medical devices known in the art; for example, by injection with a hypodermic needle.

Injectable pharmaceutical compositions of the invention may also be administered with a needleless hypodermic injection device; such as the devices disclosed in U.S. Pat. No. 5,399,163; 5,383,851; 5,312,335; 5,064,413; 4,941,880; 4,790,824 or 4,596,556.

In an embodiment of the invention, the daily dose of a "further therapeutic agent" (e.g., an anti-inflammatory agent) administered in association with the MCP1-Ig fusion (e.g., LPD1421) is, where possible, administered accordance with the *Physicians' Desk Reference* 2003 (*Physicians' Desk Reference*, 57th Ed); Medical Economics Company; ISBN: 1563634457; 57th edition (November 2002). The proper dosage can, however, be altered by a clinician to compensate for particular characteristics of the subject receiving the therapy depending, for example, on the potency of the compound administered or of MCP1-Ig fusion, side-effects, age, weight, medical condition, overall health and response.

The present invention provides methods for treating or preventing an inflammatory condition in a subject by administering, to the subject, a "therapeutically effective" amount of the MCP1-Ig fusion (e.g., LPD1421), optionally in association with a therapeutically effective amount of a further therapeutic agent. The term "therapeutically effective amount" means that amount of a therapeutic agent or substance (e.g., MCP1-Ig fusion) that will elicit a biological or medical response of a tissue, system, subject or host that is being sought by the administrator (such as a researcher, doctor or veterinarian) which includes, for example, alleviation, reversal, elimination or halting or slowing of progression of a target medical disorder or any symptom thereof to any degree including prevention of the disorder in the subject. In an embodiment of the invention, a therapeutically effective amount or dosage of MCP1-Ig fusion is from about 0.1 mpk (mg per kilogram of body weight) to about 10 mpk (e.g., 0.25, 0.5, 0.75 1, 2, 3, 4, 5, 6, 7, 8, 9, 10 mpk), e.g., once a day, every 2 days, every 4 days or every 5 days or once a week.

A composition of the invention can be administered, for example, three times a day, twice a day, once a day, three times weekly, twice weekly or once weekly, once every two weeks or 3, 4, 5, 6, 7 or 8 weeks. Moreover, the composition can be administered over a short or long period of time (e.g., 1 week, 1 month, 1 year, 5 years)

Dosage regimens can be adjusted to provide the optimum desired response (e.g., a therapeutic response). For example, the dose can be reduced or increased as indicated by exigencies of the therapeutic situation. For example, dosage can be adjusted, by a practitioner of ordinary skill in the art (e.g., physician or veterinarian) according to the drug's efficacy, progression or persistence of the disease or any of its symptoms or the patient's age, weight, height, past medical history, present medications and the potential for cross-reaction, allergies, sensitivities and adverse side-effects.

A physician or veterinarian having ordinary skill in the art can readily determine and prescribe the effective amount of the pharmaceutical composition required. For example, the physician or veterinarian could start doses of MCP1-Ig fusion (e.g., LPD1421) or a pharmaceutical composition thereof at levels lower than that required in order to achieve the desired therapeutic effect and gradually increase the dosage until the desired effect is achieved.

For example, psoriasis progress can be monitored, by the physician or veterinarian by a variety of methods, and the dosing regimen can be altered accordingly. Methods by which to monitor psoriasis include, for example, by skin biopsy, or scraping and culture of skin patches, monitoring the spread of the condition on the skin of the subject or by an X-ray to check for psoriatic arthritis if joint pain is present and persistent.

For example, rheumatoid arthritis progress can be monitored, by the physician or veterinarian, by a variety of methods, and the dosing regimen can be altered accordingly. Methods by which to monitor rheumatoid arthritis include, for example, monitoring joint mobility, joint X-rays, a rheumatoid factor blood test, checking for elevated erythrocyte sedimentation rate (ESR), a complete blood count to check for low hematocrit (anemia) or abnormal platelet counts, a blood test to check for C-reactive protein or synovial fluid analysis.

For example, Crohn's disease progress can be monitored, by the physician or veterinarian, by a variety of methods, and the dosing regimen can be altered accordingly. Methods by which to monitor Crohn's disease include, for example, monitoring the severity of symptoms reported by the subject or patient, sigmoidoscopy, colonoscopy, ERCP (endoscopic retrograde cholangiopancreatography), endoscopic ultrasound, capsule endoscopy, plain X-rays, X-rays with contrast, CT Scan or white blood cell scan.

For example, uveitis progress can be monitored, by the physician or veterinarian, by a variety of methods, and the dosing regimen can be altered accordingly. Methods by which to monitor uveitis include, for example, examination of the eye with a slit lamp microscope and ophthalmoscopy, measuring visual acuity and measuring intraocular pressure.

For example, ulcerative colitis progress can be monitored, by the physician or veterinarian, by a variety of methods, and the dosing regimen can be altered accordingly. Methods by which to monitor ulcerative colitis include, for example, routine check-ups, colonoscopies, rectal or colon biopsy, stool testing for blood or pus, blood tests to examine white blood cell levels or X-ray examination.

For example, multiple sclerosis (MS) progress can be monitored, by the physician or veterinarian, by a variety of methods, and the dosing regimen can be altered accordingly. Methods by which to monitor MS include, for example MRI (magnetic resonance imaging) scans with intravenous gadolinium to monitor lesions in the brain (plaques); electrophysiological testing, evoked potentials, to examine the impulses traveling through the nerves to determine if the impulses are moving normally or too slowly; examining the cerebro-spinal fluid that surrounds the brain and spinal cord to identify abnormal chemicals (antibodies) or cells characteristic of multiple sclerosis; or monitoring physical manifestations of MS, e.g., Romberg's sign; gait and coordination, the presence of intention tremor; the heel/shin test; L'Hermittes sign; optic neuritis; hearing loss; muscle strength; reflexes; Babinski's sign; Chaddock's sign; Hoffman's sign; doll's eye sign; sensory perception in certain parts of the body.

Type 2 Diabetes progress can be monitored by plasma glucose levels and HbA1C Insulin resistance progress can be monitored by levels of plasma glucose and insulin, respectively.

Atherosclerosis progress can be monitored by imaging of the size and the number of plaques in a given area of specific arteries.

EXAMPLES

The following examples are provided to more clearly describe the present invention and should not be construed to limit the scope of the invention. Any method or composition (e.g., polypeptides and polynucleotides) disclosed in the Examples section constitute part of the present invention.

Example 1

Cloning, Expression, and Purification of LPD1421, LPD1422, and Prototype Constructs NGSD and GSD Human MCP-1-human IgG1 (hMCP-1-hIg) was designed by fusion of human MCP-1 (Genbank accession No. NP_002973.1) to wild-type human IgG1 constant region (Fc) including the hinge, the CH2 and the CH3 regions (Genbank accession No. P01857.1). In the construct designated NGSD, the human MCP-1 was directly connected at its carboxy-terminus to the human IgG1 Fc. In the construct designated GSD, a glycine-serine dipeptide was inserted between the hMCP-1 and the IgG1 Fc. The cDNA of each construct was cloned into pTT5 expression vector and the resulting plasmid was transfected into HEK293-6E cells according to the following protocol:

The plasmid DNA was used at 1 µg/mL of culture with a DNA:PEI ratio of 1:2 w/w). The PEI reagent was prepared as a 1 mg/ml stock in water with the pH adjusted to 7.0. The DNA was added to 5% culture volume of F17 medium (Invitrogen) and then filtered through a 0.22 µm filter. PEI was added to 5% culture volume of F17 medium, followed by mixing with the DNA and incubation at room temperature for 15 minutes. The transfection mix was then added to the cells at $1.5-2 \times 10^6$ cells/ml. On the following day, TN1 hydrolysate (OrganoTechnie, LaCourneuve, France) was added to 0.5%.

Conditioned medium was harvested after 5-7 days, concentrated, and the product protein was purified by Protein-A affinity chromatography. The purified protein was dialyzed into phosphate-buffered saline, pH 7.2, and stored at 4° C.

Mature LPD1421 (mature polypeptide sequence of LPD1421 (the D265A mutation is in bold faced font; the linker is underscored, SEQ ID 16):

QPDAINAPVTCCYNFTNRKISVQRLASYRRITSSKCPKEAVIFKTIVAKEICADPKQKWVQDSMDHLDKQTQTPK

TGGEPKSSDKTHTCPPCPAPELLGGPSVFLFPPKPKDTLMISRTPEVICVVVAVSHEDPEVKFNWYVDGVEVHNA

KTKPREEQYNSTYRVVSVLTVLHQDWLNGKEYKCKVSNKALPAPIEKTISKAKGQPREPQVYTLPPSRDELTKNQ

-continued

VSLTCLVKGFYPSDIAVEWESNGQPENNYKTTPPVLDSDGSFFLYSKLTVDKSRWQQGNVFSCSVMHEALHNHYT

QKSLSLSPGK;

and, mature polypeptide sequence of LPD1422, with linker sequence of SEQ ID NO: 13:

QPDAINAPVTCCYNFTNRKISVQRLASYRRITSSKCPKEAVIEKTIVAKEICADPKQKWVQDSMDHLDKQTQTPK

T<u>GGGEPKSS</u>DKTHTCPPCPAPELLGGPSVFLFPPKPKDTLMISRTPEVTCVVVAVSHEDPEVKFNWYVDGVEVHN

AKTKPREEQYNSTYRVVSVLTVLHQDWLNGKEYKCKVSNKALPAPIEKTISKAKGQPREPQVYTLPPSRDELTKN

QVSLTCLVKGFYPSDIAVEWESNGQPENNYKTTPPVLDSDGSFFLYSKLTVDKSRWQQGNVFSCSVMHEALHNHY

TQKSLSLSPGK)

were generated from parental huMCP-1-huIgG1 by site-directed mutagenesis targeting the linker region. As was done for the parental protein, the cDNA was cloned and transfected into the HEK293 cells using Mirus TransIT-293 Reagent (Fisher Cat. #MIR 2706) according to the manufacturer's suggested protocol. Conditioned medium was harvested after 5 days, concentrated, and proteins purified using Protein-A.

For optimization of expression, the cDNAs of LPD1421 and LPD1422 were modified by codon optimization (GeneArt, Burlingame, Calif.) and the sequences are shown below:

cDNA sequence of LPD1421 (codon optimized by GeneArt), including the sequence encoding the leader polypeptide; the linker region is underscored; the initiation and the stop codons are in bold):

(SEQ ID NO: 18)

atgaaggtgtccgccgctctgctgtgtctgctgctgatcgccgccactttcatccctcagggcctggcccagcctgacgccatc aacgcccctgtgacctgctgctacaacttcaccaaccggaagatctccgtgcagcggctggcctcctaccggcggatcacc tcctccaagtgccctaaagaagccgtgatcttcaagaccatcgtggccaaagagatctgcgccgaccctaagcagaaatg ggtgcaggactccatggaccacctggacaagcagacccagacccctaagacc<u>ggcggagagcctaagtcctccg</u>aca agacccacacctgtcctccctgtcctgctcctgagctgctgggcggacttccgtgttcctgttccctccaaagcctaaggaca ccctgatgatctcccggacccctgaagtgacatgcgtggtggtggccgtgtctcacgaggatcccgaagtgaagttcaattg gtacgtggacggcgtggaggtgcacaacgccaagaccaagcctcgggaggaacagtacaactccacctaccgggtggt gtccgtgctgaccgtgctgcaccaggactggctgaacggcaaagagtacaagtgcaaggtctccaacaaggccctgcctg cccctatcgaaaagaccatctccaaggccaagggccagcctcgggaacctcaggtgtacaccctgcctcccagcaggga cgagctgaccaagaaccaggtgtccctgacctgcctggtgaagggcttctacccttccgatatcgccgtggagtgggagtct aacggccagcctgagaacaactacaagaccacccctcctgtgctggactccgacggctccttcttcctgtactccaaactga ccgtggacaagtcccggtggcagcagggcaacgtgttcctcctgctccgtgatgcacgaggccctgcacaaccactacacc cagaagtccctgtccctgtctcccggcaagtga cDNA sequence of LPD1422 (modified from LPD1421 codon optimized cDNA, including the sequence encoding the leader polypeptide; the linker region is underscored; the initiation and the stop codons are in bold):

(SEQ ID NO: 19)

atgaaggtgtccgccgctctgctgtgtctgctgctgatcgccgccactttcatccctcagggcctggcccagcctgacgccatc aacgcccctgtgacctgctgctacaacttcaccaaccggaagatctccgtgcagcggctggcctcctaccggcggatcacc tcctccaagtgccctaaagaagccgtgatcttcaagaccatcgtggccaaagagatctgcgccgaccctaagcagaaatg ggtgcaggactccatggaccacctggacaagcagacccagacccctaagacc<u>ggcggagggcgagcctaagtcctccg</u> acaagacccacacctgtcctccctgtcctgctcctgagctgctgggcggacttccgtgttcctgttccctccaaagcctaagg acaccctgatgatctcccggacccctgaagtgacatgcgtggtggtggccgtgtctcacgaggatcccgaagtgaagttca attggtacgtggacggcgtggaggtgcacaacgccaagaccaagcctcgggaggaacagtacaactccacctaccggg -continued

```
tggtgtccgtgctgaccgtgctgcaccaggactggctgaacggcaaagagtacaagtgcaaggtctccaacaaggccctg cctgccctatcgaaaagaccatctccaaggccaagggccagcctcgggaacctcaggtgtacaccctgcctcccagca gggacgagctgaccaagaaccaggtgtccctgacctgcctggtgaagggcttctaccttccgatatcgccgtggagtggg agtctaacggccagcctgagaacaactacaagaccacccctcctgtgctggactccgacggctccttcttcctgtactccaa actgaccgtggacaagtcccggtggcagcagggcaacgtgttctcctgctccgtgatgcacgaggccctgcacaaccact acacccagaagtccctgtccctgtctcccggcaagtga
```

Example 2

Chemotaxis

In this example, the presence of the variants of hMCP1-hIg was demonstrated to impede the ability of THP-1 human monocytic cells to migrate toward a recombinant human MCP1 gradient. THP-1 cells (ATCC TIB202) were maintained in RPMI1640 supplemented with 10% fetal bovine serum, 1 mM sodium pyruvate, 4.5 g/liter glucose, 1.5 g/l sodium bicarbonate, 10 mM HEPES, 0.05 mM beta-mercaptoethanol, and penicillin/streptomycin. Cell migration assays were performed using 96-well ChemoTx microplates with an 8 μm filter (NeuroProbe, Gathersburg, Md.) according to the manufacturer's instructions. For agonist assays, serially diluted recombinant human MCP-1 (rhMCP-1) (R & D Systems, Minneapolis, Minn.) or hMCP-1-hIg variants were placed in the bottom chamber. Cells were dispensed in the top wells. The microplates were placed in a 37° C. humidified $CO_2$ (5%) incubator for 2 hours to allow the cells to migrate toward human MCP-1 or the hMCP-1-hIg variants in the bottom chamber. Cell migration was quantitated as relative luminescent units (RLU) by CellTiter-Glo Luminiscent Cell Viability Assay Kit (Promega, Madison, Wis.) according to the manufacturer's protocol. The relative % of migration was calculated by GraphPad Prism 4 software (GraphPad Software, La Jolla, Calif.) using the highest number of cell migration induced by hMCP-1 as 100%. For antagonist assays, serially diluted recombinant rhMCP-1) was placed in the bottom chamber. hMCP-1-hIg variant was placed in both the top and the bottom chambers. Cells were pre-treated with the same hMCP-1-hIg variant for approximately 30 minutes and washed with medium to remove from the protein, followed by being dispensed in the top wells. The microplates were placed in a 37° C. humidified $CO_2$ (5%) incubator for 2 hours to allow the cells to migrate toward human MCP1 in the bottom chamber. Cell migration was quantitated as relative luminescent units (RLU) by CellTiter-Glo Luminiscent Cell Viability Assay Kit (Promega, Madison, Wis.) according to the manufacturer's protocol. The relative % of migration was calculated by using the highest number of cell migration as 100%. Each test concentration was carried out in triplicates or quadruplicates.

Both NGSD and GSD were detected with agonist activity. Although the $EC_{50}$ (0.03-0.3 nM) was comparable to that of the rhMCP-1, the maximal response of the cells was significantly less (Tables 1 and 2; below).

Interestingly, both LPD1421 and LPD1422 retained maximal responses of cell migration similar to that of rhMCP-1 (Table 3; below). This was apparently related to the designed linkers used in the two constructs. The agonist activity of LPD1421 and LPD1422 were comparable to that of rhMCP-1. The $EC_{50}$ values of LPD1421, LPD1422, and rhMCP-1 were approximated to be 0.03 nM, 0.1 nM, and 0.1 nM, respectively. LPD1421 appeared to be about 3-fold more potent than the parental chemokine.

The restoration of maximal response in agonist activity is important considering the circulating MCP1-Ig fusion having full-strength to attract the MCP1 receptor-bearing cells already infiltrated to egress from the tissues. This will be particularly useful in promoting the regression of atherosclerotic plaques by reducing the mass of fat-loaded macrophages in such tissues.

Furthermore, the antagonist activity of LPD1421 and LPD1422 via desensitizing CCR2-bearing cells was determined. The $IC_{50}$ of LPD1421 was estimated to be between 0.01 nM and 0.1 nM (Table 4). The $IC_{50}$ of LPD1422 was estimated to be between 0.1 and 1 nM (Table 5). The data suggested that by maintaining the serum concentration of these molecules at 1 nM or less, the circulating monocytes can be kept in a desensitized state and are blocked from the response to inflamed tissue-released MCP1 to traffick into the tissues. Such property is useful in diseases such as multiple sclerosis of which the relapsing phase is associated with infiltration of monocytes which become macrophages that cause tissue damage. Blocking of monocyte trafficking may also provide alleviation in other inflammatory diseases including rheumatoid arthritis, psoriasis, insulin resistance, and atherosclerosis.

Example 3

Stability

SEC (size-exclusion chromatography) of LPD1421 and LPD1422 in serum incubated for 4 days was assayed. Purified proteins LPD1421 or LPD1422 were labeled with DyLight-649 (Thermo Fisher Scientific, Rockford, Ill.). Following incubation at 50 μg/mL in neat human plasma at 37° C. for 4 days, samples were analyzed by size-exclusion chromatography. All samples showed no formation of high-molecular weight complex and only negligible degradation products.

Example 4

Erk Phosphorylation of LPD1421

To determine the target engagement of LPD1421, human monocytes were enriched from whole blood from two donors by negative selection using StemCell's Rosette Sep kit and following the manufacturer's procedure (Vancouver BC, Canada). The enriched cells were seeded into 12 well tissue culture treated culture plates (Falcon) @$1\times10^6$ cells/2 ml assay medium (RPMI 1640 with Glutamax (Invitrogen, Carlsbad, Calif.), 5% heat inactivated Fetal Calf Serum (Gemini, West Sacramento, Calif.), 10 mM HEPES (Hyclone, Logan, Utah) and Pen-Strep (Invitrogen) and allowed to adhere for 2 hours under standard conditions. At the time of assay, the medium and any non-adherent cells were removed and replaced with 1 ml of fresh assay medium. LPD1421 was added at the indicated concentrations to the appropriate wells and the plates were incubated for 2 minutes. The medium with LPD1421 was quickly removed from the plates which were then placed on ice and gently rinsed with 1 ml ice cold 1×PBS (Invitrogen) 3 times before the addition of 100 μl ice cold Lysis 6 buffer from the R&D Enzyme-linked immunosorbent assay (ELISA) kit (Minneapolis, Minn.) with Protease Inhibitor Cocktail (Sigma, St. Louis, Mo.) and Phenylmethylsulfonyl fluoride (Sigma) added. The lysates were homogenized by passing through a pipet tip, and allowed to stand on ice for 30 minutes before centrifugation at 12,000 rpm in a TOMY High Speed Microrefrigerated Centrifuge MR150 (TOMY Tech, Fremont, Calif.) for 10 minutes at 4° C. Supernatants were transferred to clean Costar strip tubes and stored at −20° C. until assay by ELISA. Lysates were run in an R&D ERK1/2 ELISA according to manufacturer's instructions. The monocytes from both donors were shown to respond to LPD1421 treatment in a concentration-dependent manner by phosphorylation (Table 6; below).

TABLE 1

Agonist effect of NGSD on the migration of THP-1 human monocytic cells.

| Conc. (nM) | Relative % of cell migration (mean ± SD) | |
| --- | --- | --- |
| | NGSD | rhMCP-1 |
| 0 | 22.20 ± 0.33 | 22.20 ± 0.33 |
| 0.03 | 17.67 ± 0.46 | 26.52 ± 1.24 |
| 0.1 | 34.34 ± 1.22 | 46.36 ± 1.43 |
| 0.3 | 35.54 ± 1.03 | 80.21 ± 3.12 |
| 1 | 36.53 ± 2.04 | 100.00 ± 6.21 |
| 3 | 26.66 ± 4.20 | 70.30 ± 5.45 |
| 10 | 17.46 ± 1.71 | 32.79 ± 3.16 |
| 30 | 20.13 ± 2.33 | 26.38 ± 1.57 |

TABLE 2

Agonist effect of GSD on the migration of THP-1 human monocytic cells.

| Conc. (nM) | Relative % of cell migration (mean ± SD) | |
| --- | --- | --- |
| | GSD | rhMCP-1 |
| 0 | 25.65 ± 0.43 | 24.87 ± 2.25 |
| 0.03 | 22.82 ± 1.68 | 28.61 ± 3.88 |
| 0.1 | 34.45 ± 1.95 | 52.18 ± 1.63 |
| 0.3 | 41.88 ± 2.53 | 76.05 ± 4.46 |
| 1 | 58.87 ± 1.46 | 100.00 ± 3.02 |
| 3 | 53.05 ± 1.84 | 78.09 ± 2.23 |
| 10 | 34.31 ± 0.87 | 47.46 ± 4.93 |
| 30 | 23.06 ± 0.57 | 25.32 ± 1.01 |

TABLE 3

Agonist effect of LPD1421 and LPD 1422 on the migration of THP-1 human monocytic cells.

| Conc. (nM) | Relative % of cell migration (mean ± SD) | | |
| --- | --- | --- | --- |
| | LPD1421 | LPD1422 | rhMCP-1 |
| 0 | 12.71 ± 1.77 | 16.12 ± 1.42 | 16.24 ± 0.37 |
| 0.01 | 27.87 ± 0.52 | 29.29 ± 2.53 | 29.16 ± 2.62 |
| 0.03 | 63.82 ± 3.12 | 35.81 ± 6.69 | 28.72 ± 3.40 |
| 0.1 | 104.26 ± 6.37 | 52.26 ± 0.74 | 59.39 ± 7.27 |
| 0.3 | 86.17 ± 2.40 | 93.30 ± 4.64 | 87.28 ± 9.31 |
| 1 | 59.52 ± 0.19 | 113.84 ± 3.10 | 100.00 ± 7.25 |
| 3 | 33.09 ± 1.40 | 102.82 ± 0.07 | 78.42 ± 6.98 |
| 10 | 26.44 ± 2.62 | 68.24 ± 2.74 | 48.36 ± 3.70 |

TABLE 4

Antagonist effect of LPD1421 on the migration of THP-1 human monocytic cells toward rhMCP-1.

| Conc. of rhMCP-1 (nM) | Relative % of cell migration (mean ± SD) | | | |
| --- | --- | --- | --- | --- |
| | Medium only | LPD1421 1 nM | LPD1421 0.1 nM | LPD1421 0.01 nM |
| 0 | 12.57 ± 1.76 | 12.55 ± 5.10 | 9.55 ± 1.03 | 11.77 ± 1.47 |
| 0.01 | 16.25 ± 2.42 | 8.35 ± 1.57 | 9.42 ± 0.79 | 10.57 ± 1.34 |
| 0.03 | 24.24 ± 2.04 | 10.71 ± 2.38 | 10.26 ± 3.61 | 12.65 ± 2.54 |
| 0.1 | 34.76 ± 0.96 | 7.25 ± 1.38 | 12.08 ± 2.13 | 24.31 ± 1.85 |
| 0.3 | 60.74 ± 4.42 | 13.54 ± 4.94 | 15.90 ± 4.56 | 41.72 ± 3.98 |
| 1 | 100.00 ± 7.51 | 9.44 ± 2.22 | 33.69 ± 1.24 | 61.23 ± 1.98 |
| 3 | 82.14 ± 2.62 | 9.57 ± 1.35 | 39.20 ± 1.98 | 43.96 ± 1.37 |
| 10 | 59.78 ± 3.93 | 16.15 ± 3.13 | 37.94 ± 1.23 | 39.22 ± 4.61 |

TABLE 5

Antagonist effect of LPD1422 on the migration of THP-1 human monocytic cells toward rhMCP-1.

| Conc. of rhMCP-1 (nM) | Relative % of cell migration (mean ± SD) | | | |
| --- | --- | --- | --- | --- |
| | Medium only | LPD1422 1 nM | LPD1422 0.1 nM | LPD1422 0.01 nM |
| 0 | 12.73 ± 0.99 | 2.15 ± 0.28 | 4.75 ± 1.05 | 7.11 ± 1.03 |
| 0.01 | 6.44 ± 2.25 | 2.37 ± 0.38 | 4.35 ± 0.98 | 10.64 ± 3.67 |
| 0.03 | 15.01 ± 2.83 | 4.57 ± 0.94 | 8.04 ± 1.74 | 17.60 ± 8.03 |
| 0.1 | 32.05 ± 5.43 | 4.76 ± 0.52 | 16.92 ± 5.80 | 28.72 ± 0.72 |
| 0.3 | 67.49 ± 2.02 | 4.45 ± 0.54 | 33.69 ± 3.17 | 53.43 ± 3.11 |
| 1 | 100.00 ± 4.56 | 5.99 ± 1.08 | 73.36 ± 0.27 | 80.02 ± 2.74 |
| 3 | 96.98 ± 0.63 | 12.08 ± 1.35 | 66.39 ± 4.70 | 70.26 ± 2.75 |
| 10 | 75.53 ± 1.06 | 18.92 ± 0.81 | 48.19 ± 0.32 | 42.42 ± 1.07 |

TABLE 6

Erk Phosphorylation of human monocytes by LPD1421

| Treatment | Phosphorylated Erk (ng/ml, mean ± SD) | |
| --- | --- | --- |
| | Donor 1 | Donor 2 |
| Control hIgG, 3 nM | 0 | 0 |
| LPD1421, 0.03 nM | 0 | 0 |
| LPD1421, 0.1 nM | 4.85 ± 0.56 | 3.33 ± 1.17 |
| LPD1421, 0.3 nM | 11.05 ± 0.33 | 4.63 ± 0.22 |
| LPD1421, 1 nM | 15.70 ± 0.68 | 8.90 ± 0.32 |
| LPD1421, 3 nM | 42.13 ± 1.65 | 12.75 ± 0.90 |

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Patents, patent applications, publications, product descriptions, and protocols are cited throughout this application, the disclosures of which are incorporated herein by reference in their entireties for all purposes.

We claim:

1. An isolated polypeptide comprising an MCP1 polypeptide that comprises the amino acid sequence set forth in SEQ ID NO: 17; fused to a polypeptide linker, that comprises an amino acid sequence which is a member selected from the group consisting of SEQ ID NOs: 1-13; fused to a human immunoglobulin gamma-1 polypeptide comprising the immunoglobulin hinge to the immunoglobulin CH3 region that comprises the amino acid sequence set forth in SEQ ID NO: 15.

2. The polypeptide of claim 1 comprising the amino acid sequence:

```
                                                          (SEQ ID NO: 20)
MKVSAALLCLLLIAATFIPQGLAQPDAINAPVTCCYNFTNRKISVQRLASYRRITSSKCPKEAVIFKTIVAKEIC

ADPKQKWVQDSMDHLDKQTQTPKT

GGEPKSS

DKTHTCPPCPAPELLGGPSVFLFPPKPKDTLMISRTPEVTCVVVAVSHEDPEVKFNWYVDGVEVHNAKTKPREEQ

YNSTYRVVSVLTVLHQDWLNGKEYKCKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQGNVFSCSVMHEALHNHYTQKSLSLSP

GK.
```

3. The polypeptide of claim 1 comprising the amino acid sequence:

```
                                                          (SEQ ID NO: 16)
QPDAINAPVT CCYNFTNRKI SVQRLASYRR ITSSKCPKEA VIFKTIVAKE ICADPKQKWV

QDSMDHLDKQ TQTPKTGGEPKSSD KTHTCPPCPA PELLGGPSVF LFPPKPKDTL MISRTPEVTC

VVVAVSHEDP EVKFNWYVDG VEVHNAKTKP REEQYNSTYR VVSVLTVLHQ DWLNGKEYKC

KVSNKALPAP IEKTISKAKG QPREPQVYTL PPSRDELTKN QVSLTCLVKG FYPSDIAVEW

ESNGQPENNY KTTPPVLDSD GSFFLYSKLT VDKSRWQQGN VFSCSVMHEA LHNHYTQKSL

SLSPGK.
```

4. A pharmaceutical composition comprising the polypeptide of claim 1 and a pharmaceutically acceptable carrier.

5. A composition comprising the polypeptide of claim 1 in association with one or more further therapeutic agents.

6. The composition of claim 5 wherein the further therapeutic agent is a member selected from the group consisting of aspirin, diclofenac, diflunisal, etodolac, fenoprofen, floctafenine, flurbiprofen, ibuprofen, indomethacin, ketoprofen, ketorolac, meclofenamate, mefenamic acid, meloxicam, nabumetone, naproxen, oxaprozin, phenylbutazone, piroxicam, salsalate, sulindac, tenoxicam, tiaprofenic acid, tolmetin, betamethasone benzoate, betamethasone valerate, clobetasol propionate, desoximetasone, fluocinolone acetonide, flurandrenolide, a topical steroid, alclometasone dipropionate, aloe vera, amcinonide, amcinonide, anthralin, betamethasone dipropionate, betamethasone valerate, calcipotriene, clobetasol propionate, coal tar, Dead Sea salts, desonide, desonide; betamethasone valerate, desoximetasone, diflorasone diacetate, epsom salts, fluocinolone acetonide, fluocinonide, flurandrenolide, fluticasone propionate, halcinonide, halobetasol propionate, hydrocortisone valerate, hydrocortisone, mometasone furoate, oilated oatmeal, petroleum jelly, prednicarbate, salicylic acid, tazarotene, triamcinolone acetonide, a mixture of hydrocortisone, dexamethasone, methylprednisolone and prednisolone, alefacept, etanercept, cyclosporine, methotrexate, acitretin, isotretinoin, hydroxyurea, mycophenolate mofetil, sulfasalazine, 6-Thioguanine, anakinra, injectable gold, penicillamine, azathioprine, chloroquine, hydroxychloroquine, sulfasalazine, oral gold, auranofin, gold sodium thiomalate, aurothioglucose, mesalamine, sulfasalazine, budesonide, metronidazole, ciprofloxacin, azathioprine, 6-mercaptopurine or dietary supplementation of calcium, folate, vitamin B12, celecoxib, rofecoxib, valdecoxib, lumiracoxib, etoricoxib, efalizumab, adalimumab, infliximab, rituximab, tocilizumab and ABX-IL8.

7. The polypeptide of claim 1 wherein the linker comprises the amino acid sequence set forth in SEQ ID NO: 12.

8. A method for decreasing MCP-1 mediated migration of MCP-1 receptor-bearing cells into inflamed tissue,
in a subject with rheumatoid arthritis, comprising
administering, to the subject, a therapeutically effective amount of the polypeptide of claim 1 or a pharmaceutical composition thereof optionally in association with a further therapeutic agent or procedure.

9. The method of claim 8 wherein the subject is a human.

10. The method of claim 8 wherein the further therapeutic agent or procedure is a member selected from the group consisting of denosumab, aspirin, diclofenac, diflunisal, etodolac, fenoprofen, floctafenine, flurbiprofen, ibuprofen, indomethacin, ketoprofen, ketorolac, meclofenamate, mefenamic acid, meloxicam, nabumetone, naproxen, oxaprozin, phenylbutazone, piroxicam, salsalate, sulindac, tenoxicam, tiaprofenic acid, tolmetin, betamethasone benzoate, betamethasone valerate, clobetasol propionate, desoximetasone, fluocinolone acetonide, flurandrenolide, a topical steroid, alclometasone dipropionate, aloe vera, amcinonide, amcinonide, anthralin, betamethasone dipropionate, betamethasone valerate, calcipotriene, clobetasol propionate, coal tar, Dead Sea salts, desonide, desonide; betamethasone valerate, desoximetasone, diflorasone diacetate, epsom salts, fluocinolone acetonide, fluocinonide, flurandrenolide, fluticasone propionate, halcinonide, halobetasol propionate, hydrocortisone valerate, hydrocortisone, mometasone furoate, oilated oatmeal, petroleum jelly, prednicarbate, salicylic acid, tazarotene, triamcinolone acetonide, a mixture of hydrocortisone, dexamethasone, methylprednisolone and prednisolone, alefacept, etanercept, cyclosporine, methotrexate, acitretin, isotretinoin, hydroxyurea, mycophenolate mofetil, sulfasalazine, 6-Thioguanine, anakinra, injectable gold, penicillamine, azathioprine, chloroquine, hydroxychloroquine, sulfasalazine, oral gold, auranofin, gold sodium thiomalate, aurothioglucose, mesalamine, sulfasalazine, budesonide, metronidazole, ciprofloxacin, azathioprine, 6-mercaptopurine or dietary supplementation of calcium, folate, vitamin B12, celecoxib, rofecoxib, valdecoxib, lumiracoxib, etoricoxib, efalizumab, adalimumab, infliximab, rituximab, tocilizumab, ABX-IL8 and phototherapy.

* * * * *

```
                              SEQUENCE LISTING

<160> NUMBER OF SEQ ID NOS: 22

<210> SEQ ID NO 1
<211> LENGTH: 6
<212> TYPE: PRT
<213> ORGANISM: Artificial Sequence
<220> FEATURE:
<223> OTHER INFORMATION: linker

<400> SEQUENCE: 1

Val Glu Pro Lys Ser Cys
1               5

<210> SEQ ID NO 2
<211> LENGTH: 8
<212> TYPE: PRT
<213> ORGANISM: Artificial Sequence
<220> FEATURE:
<223> OTHER INFORMATION: linker

<400> SEQUENCE: 2

Gly Ser Val Glu Pro Lys Ser Cys
1               5

<210> SEQ ID NO 3
<211> LENGTH: 7
<212> TYPE: PRT
<213> ORGANISM: Artificial Sequence
<220> FEATURE:
<223> OTHER INFORMATION: linker

<400> SEQUENCE: 3

Gly Ser Glu Pro Lys Ser Cys
1               5

<210> SEQ ID NO 4
<211> LENGTH: 8
<212> TYPE: PRT
<213> ORGANISM: Artificial Sequence
<220> FEATURE:
<223> OTHER INFORMATION: linker

<400> SEQUENCE: 4

Gly Ser Gly Glu Pro Lys Ser Cys
1               5

<210> SEQ ID NO 5
<211> LENGTH: 9
<212> TYPE: PRT
<213> ORGANISM: Artificial Sequence
<220> FEATURE:
<223> OTHER INFORMATION: linker

<400> SEQUENCE: 5

Gly Ser Gly Ser Glu Pro Lys Ser Cys
1               5

<210> SEQ ID NO 6
<211> LENGTH: 7
<212> TYPE: PRT
<213> ORGANISM: Artificial Sequence
<220> FEATURE:
<223> OTHER INFORMATION: linker
```

```
<400> SEQUENCE: 6

Gly Gly Glu Pro Lys Ser Cys
1               5

<210> SEQ ID NO 7
<211> LENGTH: 8
<212> TYPE: PRT
<213> ORGANISM: Artificial Sequence
<220> FEATURE:
<223> OTHER INFORMATION: linker

<400> SEQUENCE: 7

Gly Gly Gly Glu Pro Lys Ser Cys
1               5

<210> SEQ ID NO 8
<211> LENGTH: 8
<212> TYPE: PRT
<213> ORGANISM: Artificial Sequence
<220> FEATURE:
<223> OTHER INFORMATION: linker

<400> SEQUENCE: 8

Gly Ser Val Glu Pro Lys Ser Ser
1               5

<210> SEQ ID NO 9
<211> LENGTH: 7
<212> TYPE: PRT
<213> ORGANISM: Artificial Sequence
<220> FEATURE:
<223> OTHER INFORMATION: linker

<400> SEQUENCE: 9

Gly Ser Glu Pro Lys Ser Ser
1               5

<210> SEQ ID NO 10
<211> LENGTH: 8
<212> TYPE: PRT
<213> ORGANISM: Artificial Sequence
<220> FEATURE:
<223> OTHER INFORMATION: linker

<400> SEQUENCE: 10

Gly Ser Gly Glu Pro Lys Ser Ser
1               5

<210> SEQ ID NO 11
<211> LENGTH: 9
<212> TYPE: PRT
<213> ORGANISM: Artificial Sequence
<220> FEATURE:
<223> OTHER INFORMATION: linker

<400> SEQUENCE: 11

Gly Ser Gly Ser Glu Pro Lys Ser Ser
1               5

<210> SEQ ID NO 12
<211> LENGTH: 7
<212> TYPE: PRT
<213> ORGANISM: Artificial Sequence
<220> FEATURE:
<223> OTHER INFORMATION: linker

<400> SEQUENCE: 12
```

```
Gly Gly Glu Pro Lys Ser Ser
1               5

<210> SEQ ID NO 13
<211> LENGTH: 8
<212> TYPE: PRT
<213> ORGANISM: Artificial Sequence
<220> FEATURE:
<223> OTHER INFORMATION: linker

<400> SEQUENCE: 13

Gly Gly Gly Glu Pro Lys Ser Ser
1               5

<210> SEQ ID NO 14
<211> LENGTH: 99
<212> TYPE: PRT
<213> ORGANISM: Homo sapiens

<400> SEQUENCE: 14

Met Lys Val Ser Ala Ala Leu Leu Cys Leu Leu Ile Ala Ala Thr
1               5                   10                  15

Phe Ile Pro Gln Gly Leu Ala Gln Pro Asp Ala Ile Asn Ala Pro Val
                20                  25                  30

Thr Cys Cys Tyr Asn Phe Thr Asn Arg Lys Ile Ser Val Gln Arg Leu
            35                  40                  45

Ala Ser Tyr Arg Arg Ile Thr Ser Ser Lys Cys Pro Lys Glu Ala Val
        50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr

<210> SEQ ID NO 15
<211> LENGTH: 227
<212> TYPE: PRT
<213> ORGANISM: Homo sapiens

<400> SEQUENCE: 15

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Ala Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
        130                 135                 140

Leu Thr Cys Leu Val Lys Gly Phe Tyr Pro Ser Asp Ile Ala Val Glu
```

```
                145                 150                 155                 160
Trp Glu Ser Asn Gly Gln Pro Glu Asn Asn Tyr Lys Thr Thr Pro Pro
                    165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
            210                 215                 220

Pro Gly Lys
225

<210> SEQ ID NO 16
<211> LENGTH: 310
<212> TYPE: PRT
<213> ORGANISM: Homo sapiens

<400> SEQUENCE: 16

Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
                20                  25                  30

Ser Ser Lys Cys Pro Lys Glu Ala Val Ile Phe Lys Thr Ile Val Ala
            35                  40                  45

Lys Glu Ile Cys Ala Asp Pro Lys Gln Lys Trp Val Gln Asp Ser Met
        50                  55                  60

Asp His Leu Asp Lys Gln Thr Gln Thr Pro Lys Thr Gly Gly Glu Pro
65                  70                  75                  80

Lys Ser Ser Asp Lys Thr His Thr Cys Pro Pro Cys Pro Ala Pro Glu
                85                  90                  95

Leu Leu Gly Gly Pro Ser Val Phe Leu Phe Pro Pro Lys Pro Lys Asp
            100                 105                 110

Thr Leu Met Ile Ser Arg Thr Pro Glu Val Thr Cys Val Val Val Ala
        115                 120                 125

Val Ser His Glu Asp Pro Glu Val Lys Phe Asn Trp Tyr Val Asp Gly
130                 135                 140

Val Glu Val His Asn Ala Lys Thr Lys Pro Arg Glu Glu Gln Tyr Asn
145                 150                 155                 160

Ser Thr Tyr Arg Val Val Ser Val Leu Thr Val Leu His Gln Asp Trp
                165                 170                 175

Leu Asn Gly Lys Glu Tyr Lys Cys Lys Val Ser Asn Lys Ala Leu Pro
            180                 185                 190

Ala Pro Ile Glu Lys Thr Ile Ser Lys Ala Lys Gly Gln Pro Arg Glu
        195                 200                 205

Pro Gln Val Tyr Thr Leu Pro Pro Ser Arg Asp Glu Leu Thr Lys Asn
210                 215                 220

Gln Val Ser Leu Thr Cys Leu Val Lys Gly Phe Tyr Pro Ser Asp Ile
225                 230                 235                 240

Ala Val Glu Trp Glu Ser Asn Gly Gln Pro Glu Asn Asn Tyr Lys Thr
                245                 250                 255

Thr Pro Pro Val Leu Asp Ser Asp Gly Ser Phe Phe Leu Tyr Ser Lys
            260                 265                 270

Leu Thr Val Asp Lys Ser Arg Trp Gln Gln Gly Asn Val Phe Ser Cys
        275                 280                 285

Ser Val Met His Glu Ala Leu His Asn His Tyr Thr Gln Lys Ser Leu
```

```
                290               295               300
Ser Leu Ser Pro Gly Lys
305                310

<210> SEQ ID NO 17
<211> LENGTH: 72
<212> TYPE: PRT
<213> ORGANISM: Homo sapiens

<400> SEQUENCE: 17

Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
                20                  25                  30

Ser Ser Lys Cys Pro Lys Glu Ala Val Ile Phe Lys Thr Ile Val Ala
            35                  40                  45

Lys Glu Ile Cys Ala Asp Pro Lys Gln Lys Trp Val Gln Asp Ser Met
        50                  55                  60

Asp His Leu Asp Lys Gln Thr Gln
65                  70

<210> SEQ ID NO 18
<211> LENGTH: 1002
<212> TYPE: DNA
<213> ORGANISM: Homo sapiens

<400> SEQUENCE: 18
atgaaggtgt ccgccgctct gctgtgtctg ctgctgatcg ccgccacttt catccctcag      60
ggcctggccc agcctgacgc catcaacgcc ctgtgacct gctgctacaa cttcaccaac      120
cggaagatct ccgtgcagcg gctggcctcc taccggcgga tcacctcctc caagtgccct     180
aaagaagccg tgatcttcaa gaccatcgtg gccaaagaga tctgcgccga ccctaagcag     240
aaatgggtgc aggactccat ggaccacctg gacaagcaga cccagacccc taagaccggc     300
ggagagccta gtcctccga caagaccac acctgtcctc cctgtcctgc tcctgagctg      360
ctgggcggac cttccgtgtt cctgttccct ccaaagccta ggacaccct gatgatctcc      420 cggaccctg aagtgacatg cgtggtggtg gccgtgtctc acgaggatcc cgaagtgaag      480
ttcaattggt acgtggacgg cgtggaggtg cacaacgcca agaccaagcc tcgggaggaa     540
cagtacaact ccacctaccg ggtggtgtcc gtgctgaccg tgctgcacca ggactggctg     600
aacggcaaag agtacaagtg caaggtctcc aacaaggccc tgcctgcccc tatcgaaaag    660
accatctcca aggccaaggg ccagcctcgg gaacctcagg tgtacaccct gcctcccagc    720
agggacgagc tgaccaagaa ccaggtgtcc ctgacctgcc tggtgaaggg cttctaccct    780
tccgatatcg ccgtggagtg ggagtctaac ggccagcctg agaacaacta caagaccacc    840
cctcctgtgc tggactccga cggctccttc ttcctgtact ccaaactgac cgtggacaag    900
tcccggtggc agcagggcaa cgtgttctcc tgctccgtga tgcacgaggc cctgcacaac    960
cactacaccc agaagtccct gtccctgtct cccggcaagt ga                      1002

<210> SEQ ID NO 19
<211> LENGTH: 1005
<212> TYPE: DNA
<213> ORGANISM: Homo sapiens

<400> SEQUENCE: 19
atgaaggtgt ccgccgctct gctgtgtctg ctgctgatcg ccgccacttt catccctcag      60
```

```
ggcctggccc agcctgacgc catcaacgcc cctgtgacct gctgctacaa cttcaccaac      120
cggaagatct ccgtgcagcg gctggcctcc taccggcgga tcacctcctc caagtgccct      180
aaagaagccg tgatcttcaa gaccatcgtg gccaaagaga tctgcgccga ccctaagcag      240
aaatgggtgc aggactccat ggaccacctg gacaagcaga cccagacccc taagaccggc      300
ggaggcgagc ctaagtcctc cgacaagacc cacacctgtc ctccctgtcc tgctcctgag      360
ctgctgggcg accttccgt gttcctgttc cctccaaagc ctaaggacac cctgatgatc       420
tcccggaccc ctgaagtgac atgcgtggtg gtggccgtgt ctcacgagga tcccgaagtg      480
aagttcaatt ggtacgtgga cggcgtggag gtgcacaacg ccaagaccaa gcctcgggag      540
gaacagtaca actccaccta ccgggtggtg tccgtgctga ccgtgctgca ccaggactgg      600
ctgaacggca agagtacaa gtgcaaggtc tccaacaagg ccctgcctgc cctatcgaa       660
aagaccatct ccaaggccaa gggccagcct cgggaacctc aggtgtacac cctgcctccc      720
agcagggacg agctgaccaa gaaccaggtg tccctgacct gcctggtgaa gggcttctac      780
ccttccgata tcgccgtgga gtgggagtct aacggccagc tgagaacaa ctacaagacc       840
acccctcctg tgctggactc cgacggctcc ttcttcctgt actccaaact gaccgtggac      900
aagtcccggt ggcagcaggg caacgtgttc tcctgctccg tgatgcacga ggccctgcac      960
aaccactaca cccagaagtc cctgtccctg tctcccggca agtga                     1005
```

<210> SEQ ID NO 20
<211> LENGTH: 333
<212> TYPE: PRT
<213> ORGANISM: Homo sapiens

<400> SEQUENCE: 20

```
Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
            20                  25                  30

Thr Cys Cys Tyr Asn Phe Thr Asn Arg Lys Ile Ser Val Gln Arg Leu
        35                  40                  45

Ala Ser Tyr Arg Arg Ile Thr Ser Ser Lys Cys Pro Lys Glu Ala Val
    50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr Gly Gly Glu Pro Lys Ser Ser Asp Lys Thr His Thr Cys
            100                 105                 110

Pro Pro Cys Pro Ala Pro Glu Leu Leu Gly Gly Pro Ser Val Phe Leu
        115                 120                 125

Phe Pro Pro Lys Pro Lys Asp Thr Leu Met Ile Ser Arg Thr Pro Glu
    130                 135                 140

Val Thr Cys Val Val Val Ala Val Ser His Glu Asp Pro Glu Val Lys
145                 150                 155                 160

Phe Asn Trp Tyr Val Asp Gly Val Glu Val His Asn Ala Lys Thr Lys
                165                 170                 175

Pro Arg Glu Glu Gln Tyr Asn Ser Thr Tyr Arg Val Val Ser Val Leu
            180                 185                 190

Thr Val Leu His Gln Asp Trp Leu Asn Gly Lys Glu Tyr Lys Cys Lys
        195                 200                 205

Val Ser Asn Lys Ala Leu Pro Ala Pro Ile Glu Lys Thr Ile Ser Lys
```

```
                210                 215                 220
Ala Lys Gly Gln Pro Arg Glu Pro Gln Val Tyr Thr Leu Pro Pro Ser
225                 230                 235                 240

Arg Asp Glu Leu Thr Lys Asn Gln Val Ser Leu Thr Cys Leu Val Lys
                245                 250                 255

Gly Phe Tyr Pro Ser Asp Ile Ala Val Glu Trp Glu Ser Asn Gly Gln
                260                 265                 270

Pro Glu Asn Asn Tyr Lys Thr Thr Pro Pro Val Leu Asp Ser Asp Gly
                275                 280                 285

Ser Phe Phe Leu Tyr Ser Lys Leu Thr Val Asp Lys Ser Arg Trp Gln
290                 295                 300

Gln Gly Asn Val Phe Ser Cys Ser Val Met His Glu Ala Leu His Asn
305                 310                 315                 320

His Tyr Thr Gln Lys Ser Leu Ser Leu Ser Pro Gly Lys
                325                 330

<210> SEQ ID NO 21
<211> LENGTH: 448
<212> TYPE: PRT
<213> ORGANISM: Artificial Sequence
<220> FEATURE:
<223> OTHER INFORMATION: immunoglobulin

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Gly Ile Thr Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Gly Thr Thr Val Ile Met Ser Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
210                 215                 220

Cys Val Glu Cys Pro Pro Cys Pro Ala Pro Val Ala Gly Pro Ser
225                 230                 235                 240

Val Phe Leu Phe Pro Pro Lys Pro Lys Asp Thr Leu Met Ile Ser Arg
                245                 250                 255
```

Thr Pro Glu Val Thr Cys Val Val Asp Val Ser His Glu Asp Pro
                260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Phe Arg Val Val
290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
                325                 330                 335

Ile Ser Lys Thr Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 22
<211> LENGTH: 215
<212> TYPE: PRT
<213> ORGANISM: Artificial Sequence
<220> FEATURE:
<223> OTHER INFORMATION: immunoglobulin

<400> SEQUENCE: 22

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Gly Arg
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Phe Tyr Cys Gln Gln Tyr Gly Ser Ser Pro
                85                  90                  95

Arg Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

```
Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```